United States Patent
Charest et al.

(10) Patent No.: US 10,603,419 B2
(45) Date of Patent: Mar. 31, 2020

(54) SYSTEMS AND METHODS FOR INCREASING CONVECTIVE CLEARANCE OF UNDESIRED PARTICLES IN A MICROFLUIDIC DEVICE

(71) Applicants: The Charles Stark Draper Laboratory, Inc., Cambridge, MA (US); Johnson & Johnson Innovation LLC, Somerville, NJ (US)

(72) Inventors: Joseph L. Charest, Cambridge, MA (US); Martin Nohilly, Murray Hill, NJ (US); Christopher Dibiasio, Stoughton, MA (US); Jeffrey T. Borenstein, Newton, MA (US); Mark Laurenzi, Mountain Lakes, NJ (US); Jonathan Wilson, Mattapoisett Center, MA (US)

(73) Assignee: The Charles Stark Draper Laboratories, Inc., Cambridge, MA (US)

( * ) Notice: Subject to any disclaimer, the term of this patent is extended or adjusted under 35 U.S.C. 154(b) by 411 days.

(21) Appl. No.: 15/046,152

(22) Filed: Feb. 17, 2016

(65) Prior Publication Data

US 2016/0158428 A1     Jun. 9, 2016

Related U.S. Application Data

(63) Continuation-in-part of application No. 14/832,875, filed on Aug. 21, 2015, now Pat. No. 10,342,909, (Continued)

(51) Int. Cl.
*A61M 1/16* (2006.01)
*A61M 1/34* (2006.01)
(Continued)

(52) U.S. Cl.
CPC ............ *A61M 1/1603* (2014.02); *A61M 1/16* (2013.01); *A61M 1/1601* (2014.02); (Continued)

(58) Field of Classification Search
CPC .... A61M 1/16; A61M 1/3482; A61M 1/3403; A61M 1/3413; A61M 1/3417; (Continued)

(56) References Cited

U.S. PATENT DOCUMENTS

| 4,038,192 A | 7/1977 | Serur |
|---|---|---|
| 4,218,321 A | 8/1980 | Sasaki et al. |

(Continued)

FOREIGN PATENT DOCUMENTS

| CN | 102596373 A | 7/2012 |
|---|---|---|
| JP | S48-032397 | 3/1973 |

(Continued)

OTHER PUBLICATIONS

Final Office Action in U.S. Appl. No. 13/739,685 dated Jul. 9, 2014.
(Continued)

*Primary Examiner* — Pranav N Patel
(74) *Attorney, Agent, or Firm* — Christopher J. McKenna; Foley & Lardner LLP

(57) ABSTRACT

A microfluidic device for increasing convective clearance of particles from a fluid is provided. In some implementations, described herein the microfluidic device includes multiple layers that each define infusate, blood, and filtrate channels. Each of the channels have a pressure profile. The device can also include one or more pressure control features. The pressure control feature controls a difference between the pressure profiles along a length of the device. For example, the pressure control feature can control the difference between the pressure profile of the filtrate channel and the pressure profile of the blood channel. In some implementa- (Continued)

tions, the pressure control feature controls the pressure difference between two channels such that the difference varies along the length of the channels by less than 50% of the pressure difference between the channels at the channels' inlets.

19 Claims, 30 Drawing Sheets

Related U.S. Application Data which is a continuation-in-part of application No. 13/739,701, filed on Jan. 11, 2013, now abandoned, and a continuation-in-part of application No. 13/739,685, filed on Jan. 11, 2013, now Pat. No. 10,478,543.

(60) Provisional application No. 62/040,131, filed on Aug. 21, 2014.

(51) Int. Cl.
  *B81B 7/00* (2006.01)
  *B01D 63/08* (2006.01)
  *B01D 61/28* (2006.01)

(52) U.S. Cl.
  CPC ........ *A61M 1/1631* (2014.02); *A61M 1/1694* (2013.01); *A61M 1/34* (2013.01); *A61M 1/3403* (2014.02); *A61M 1/3434* (2014.02); *A61M 1/3437* (2014.02); *A61M 1/3441* (2013.01); *B01D 61/28* (2013.01); *B01D 63/088* (2013.01); *B81B 7/0009* (2013.01); *A61M 2202/0413* (2013.01); *A61M 2205/0244* (2013.01); *A61M 2205/3331* (2013.01); *A61M 2205/3334* (2013.01); *A61M 2230/207* (2013.01)

(58) Field of Classification Search
  CPC .............. A61M 1/3479; A61M 1/1631; A61M 1/342–3468; A61M 2205/3331; B01D 61/28; B01D 61/30; B01D 61/32; B01D 61/50; B01D 63/082; B01D 63/084; B01D 63/085; B01D 63/088; B01D 63/08; B01D 63/081; B01D 2313/08; B01D 2313/19; B01D 2311/14; B01D 2311/16; B01D 2317/04; B01D 69/06
  See application file for complete search history.

(56) References Cited

U.S. PATENT DOCUMENTS

| | | | |
|---|---|---|---|
| 4,789,468 | A | 12/1988 | Sirkar |
| 5,660,722 | A | 8/1997 | Nederlof |
| 5,730,712 | A | 3/1998 | Falkvall et al. |
| 6,277,124 | B1 | 8/2001 | Haag |
| 6,685,809 | B1 | 2/2004 | Jacobson et al. |
| 7,754,077 | B1 | 7/2010 | Singh et al. |
| 2002/0190000 | A1 | 12/2002 | Baurmeister |
| 2004/0068219 | A1 | 4/2004 | Summerton et al. |
| 2004/0084370 | A1 | 5/2004 | Singh et al. |
| 2004/0127842 | A1 | 7/2004 | Collins et al. |
| 2004/0256318 | A1* | 12/2004 | Iida ................ B01D 57/02 210/634 |
| 2005/0202557 | A1 | 9/2005 | Borenstein et al. |
| 2005/0274658 | A1 | 12/2005 | Rosenbaum et al. |
| 2008/0000539 | A1 | 1/2008 | Bivin |
| 2008/0093298 | A1 | 4/2008 | Browning et al. |
| 2008/0138596 | A1 | 6/2008 | Yoshida et al. |
| 2008/0251444 | A1 | 10/2008 | Fendya et al. |
| 2008/0318324 | A1 | 12/2008 | Chiu et al. |
| 2010/0032041 | A1 | 2/2010 | Diperna |
| 2010/0285101 | A1 | 11/2010 | Moore et al. |
| 2010/0300882 | A1 | 12/2010 | Zhang et al. |
| 2010/0326916 | A1 | 12/2010 | Wrazel et al. |
| 2011/0082563 | A1 | 4/2011 | Charest et al. |
| 2011/0155667 | A1 | 6/2011 | Charest et al. |
| 2011/0158847 | A1 | 6/2011 | Charest et al. |
| 2011/0290113 | A1 | 12/2011 | Borenstein et al. |
| 2012/0118801 | A1 | 5/2012 | Rada et al. |
| 2012/0223015 | A1 | 9/2012 | Browning et al. |
| 2012/0330214 | A1 | 12/2012 | Peters et al. |
| 2014/0197101 | A1 | 7/2014 | Harjes et al. |
| 2014/0197105 | A1 | 7/2014 | Dibiasio et al. |
| 2014/0339161 | A1 | 11/2014 | Leonard et al. |
| 2015/0076067 | A1 | 3/2015 | Borenstein et al. |

FOREIGN PATENT DOCUMENTS

| | | |
|---|---|---|
| JP | H08-192031 | 9/1995 |
| JP | H11-000394 | 1/1999 |
| WO | WO-98/09717 | 3/1998 |
| WO | WO-2011/059786 A1 | 5/2011 |
| WO | WO-2011/132164 | 10/2011 |
| WO | WO2013052951 * | 4/2013 |

OTHER PUBLICATIONS

International Preliminary Report on Patentability dated Jul. 23, 2015 in PCT Application No. PCT/S2014/010683.
International Preliminary Report on Patentability dated Jul. 23, 2015 in PCT Application No. PCT/US2014/010684.
International Search Report and Written Opinion dated Nov. 6, 2015 in PCT Application No. PCT/US2015/046383.
International Search Report and Written Opinion dated May 21, 2014 in PCT Application No. PCT/US2014/010684.
International Search Report and Written Opinion dated May 6, 2014 in PCT Application No. PCT/US2014/010683.
U.S. Office Action in U.S. Appl. No. 13/739,685 dated Nov. 5, 2015.
U.S. Office Action in U.S. Appl. No. 13/739,685 dated Mar. 12, 2015.
U.S. Office Action in U.S. Appl. No. 13/739,701 dated Aug. 14, 2015.
U.S. Office Action in U.S. Appl. No. 13/739,685 dated Jul. 6, 2015.
U.S. Office Action in U.S. Appl. No. 13/739,685 dated Nov. 5, 2013.
U.S. Office Action on U.S. Appl. No. 13/739,701 dated Mar. 16, 2016.
Vandelnder et al, "Prefusion in Microfluidic Croff-Flow: Separation of White Blood Cells from Whole Blood and Exchange of Medium in a Continuous Flow", Analytical Chemistry, vol. 79, No. 5, pp. 2023-2030, Mar. 1, 2007.
International Search Report and Written Opinion dated May 8, 2017 in PCT Application No. PCT/US2017/018169.
Office Action dated Mar. 23, 2017 in European Patent Application No. 14702347.7.
Office Action dated May 1, 2017 in U.S. Appl. No. 14/568,666.
Office Action dated May 12, 2016 in U.S. Appl. No. 13/739,685.
Office Action dated Dec. 7, 2016 in U.S. Appl. No. 13/739,685.
Office Action dated Nov. 30, 2016 in U.S. Appl. No. 13/739,701.
Non-Final Office Action on U.S. Appl. No. 14/832,875 dated Aug. 15, 2018.
Notice of Allowance on U.S. Appl. No. 14/568,666 dated Apr. 2, 2018.
Notice of Reasons for Rejections for application No. 2015-552742 dated Jan. 9, 2018.
Office Action issued on JP 2015-552743 dated Jan. 9, 2018.
Office Action on U.S. Appl. No. 13/739,685 dated Apr. 2, 2018.
Office Action on U.S. Appl. No. 13/739,685 dated Dec. 1, 2017.
Office Action on U.S. Appl. No. 13/739,685 dated Jun. 1, 2017.
Office Action on U.S. Appl. No. 13/739,685 dated May 12, 2016.
Office Action on U.S. Appl. No. 13/739,701 dated Nov. 30, 2016.
Office Action on U.S. Appl. No. 14/568,666 dated May 1, 2017.
Office Action on U.S. Appl. No. 14/568,666 dated Nov. 7, 2017.
Office Action on U.S. Appl. No. 14/832,875 dated Jan. 25, 2018.
EPO Examination report for application No. 14702347.7-1101 dated Nov. 9, 2018.

(56) References Cited

OTHER PUBLICATIONS

First Office Action for CN Patent Application No. 201580051806.6.
International Preliminary Report on Patentability for application No. PCT/US2017/018169 dated Aug. 30, 2018.
Japanese Notice of Reasons for Rejections for application No. 2015552743 dated Nov. 29, 2018.
Notice of Allowance on U.S. Appl. No. 14/832,875 dated Mar. 1, 2019.
Office Action on U.S. Appl. No. 13/739,685 dated Oct. 15, 2018.
Foreign Action other than Search Report on CN 201580051806.6 dated May 29, 2019.
Foreign Action other than Search Report on EP 14702347.7 dated Jul. 22, 2019.
Foreign Action other than Search Report on JP 2015-552743 dated Aug. 22, 2019.
Notice of Allowance on U.S. Appl. No. 13/739,685 dated Jul. 16, 2019.
Notice of Reasons for Rejection for Japanese Application No. 2017-529978 dated May 29, 2019.

\* cited by examiner

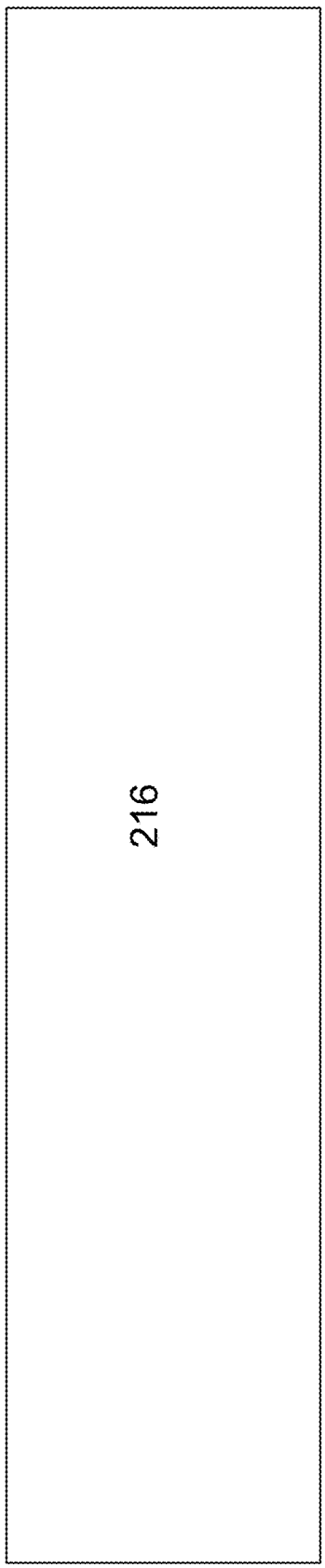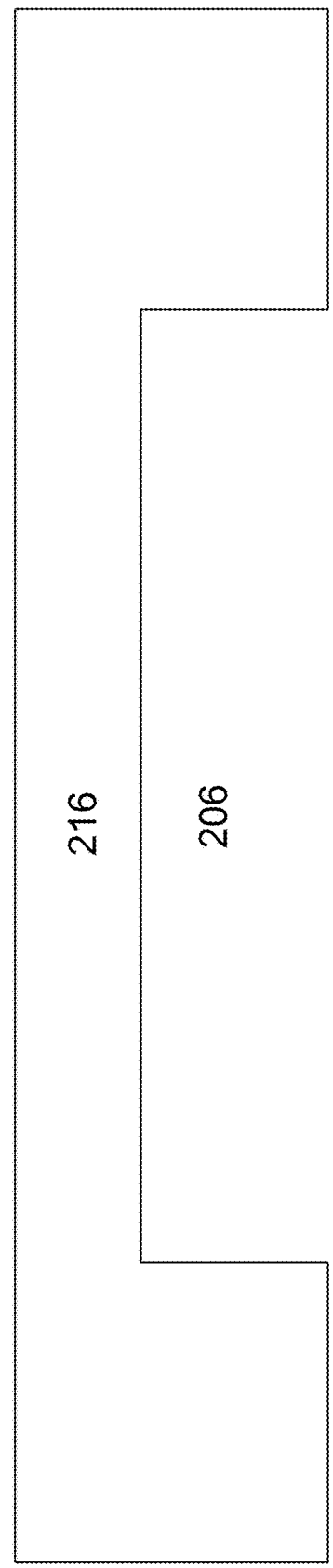

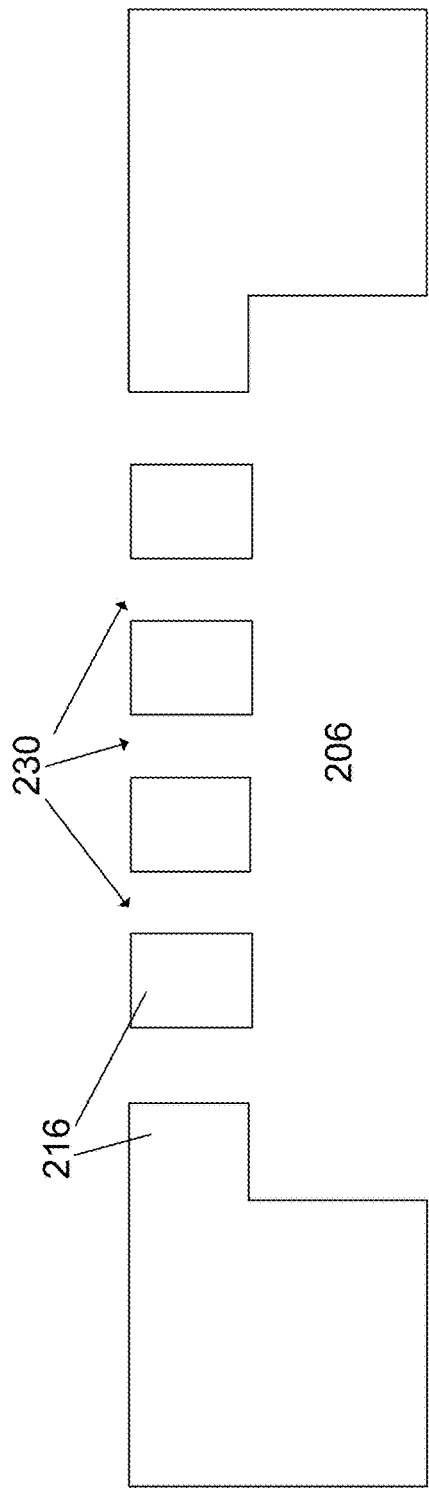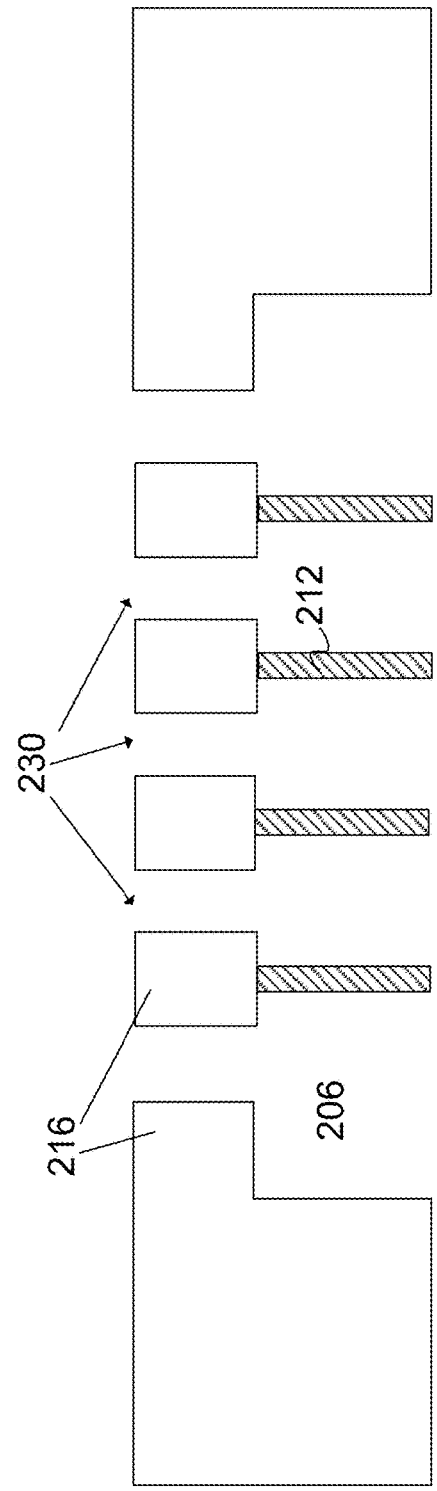

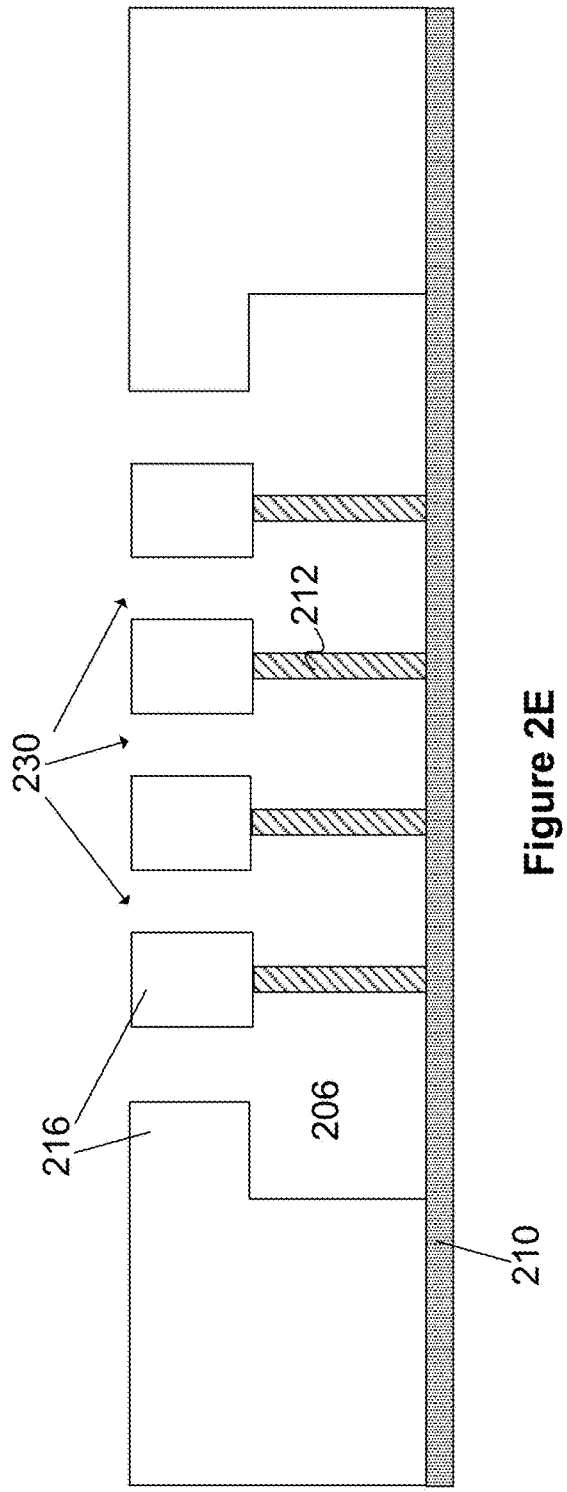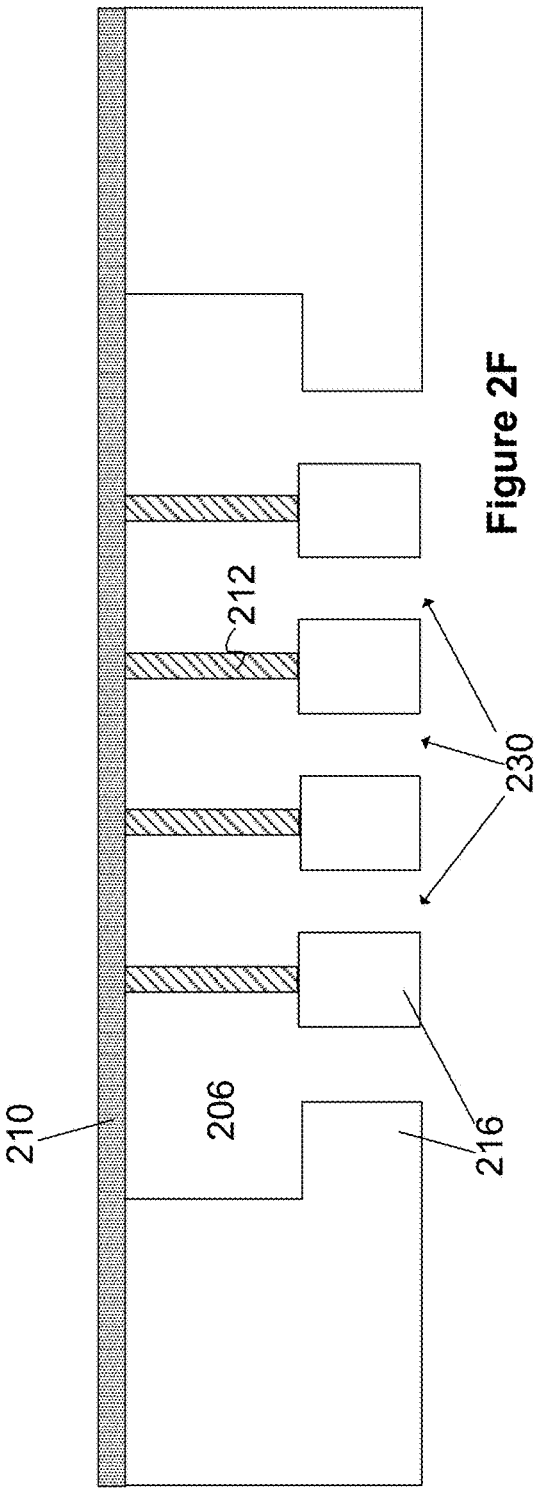

SYSTEMS AND METHODS FOR INCREASING CONVECTIVE CLEARANCE OF UNDESIRED PARTICLES IN A MICROFLUIDIC DEVICE

CROSS-REFERENCE TO RELATED APPLICATIONS

This application is a continuation in part of U.S. patent application Ser. No. 14/832,875 filed Aug. 21, 2015 and titled "SYSTEMS AND METHODS FOR INCREASING CONVECTIVE CLEARANCE OF UNDESIRED PARTICLES IN A MICROFLUIDIC DEVICE," which claims priority to and benefit of U.S. Provisional Patent Application No. 62/040,131 filed on Aug. 21, 2014 and titled "SYSTEMS AND METHODS FOR INCREASING CONVECTIVE CLEARANCE OF UNDESIRED PARTICLES IN A MICROFLUIDIC DEVICE," each of which are herein incorporated by reference in their entirety. U.S. patent application Ser. No. 14/832,875 is also a continuation in part of U.S. patent application Ser. No. 13/739,701 filed on Jan. 11, 2013 and titled "SYSTEMS AND METHODS FOR INCREASING CONVECTIVE CLEARANCE OF UNDESIRED PARTICLES IN A MICROFLUIDIC DEVICE," and a continuation in part of U.S. patent application Ser. No. 13/739,685 filed on Jan. 11, 2013 and titled "SYSTEMS AND METHODS FOR INCREASING CONVECTIVE CLEARANCE OF UNDESIRED PARTICLES IN A MICROFLUIDIC DEVICE," each of which are herein incorporated by reference in their entirety.

BACKGROUND

A dialysis device contains a series of fluid channels separated by a permeable membrane. Convective clearance of solutes from blood in the device is determined by the transmembrane pressure in the device. Typically, the fluid in adjacent channels flows in opposite directions and the channels have a non-linear fluid to red-blood cell volume profile along their lengths. Increasing the convective clearance requires decreasing the fluid to red-blood cell volume in the channel carrying blood, which can result in an unsafe hematocrit level in the channel. Therefore, it is desirable to increase the amount of convective clearance within a compact dialysis device while maintaining safe hematocrit levels throughout the blood channel.

SUMMARY OF THE DISCLOSURE

According to one aspect of the disclosure, a microfluidic device includes a first layer that defines an infusate channel. The infusate channel has a first pressure profile. The device also includes a second layer that defines a blood channel complementary to and in fluidic communication with the infusate channel. The blood channel has a second pressure profile. The device also includes a third layer defining a filtrate channel that is complementary to and in fluidic communication with the blood channel. The filtrate channel has a third pressure profile. The device also includes a first interchannel flow barrier that separates the infusate channel and the blood channel. The device includes a second interchannel flow barrier that separates the filtrate channel and the blood channel. The device includes a first controllable flow control device that is configured to actively control a slope of the third pressure profile along a length of the filtrate channel relative to the slope of the second pressure profile along the length of the blood channel. The device includes a control system that is configured to modify a state of the first controllable flow control device.

In some implementations, the control system is configured to achieve an operational state where the slope of the third pressure profile is greater than the slope of the second pressure profile. In other implementations, the control system is configured to achieve an operational state where the slope of the third pressure profile is less than the slope of the second pressure profile. In other implementations, the control system is configured to achieve an operational state where the slope of the third pressure profile is substantially parallel to the slope of the second pressure profile.

In some implementations, the first controllable flow control device is configured such that a pressure difference along a length of the blood channel and the filtrate channel does not vary by more than 50% of an average pressure difference between the blood channel and the filtrate channel. In some implementations, the control system is configured to control the first controllable flow control device to maintain a pressure difference between a pressure of a first fluid flowing through the blood channel and a pressure of a second fluid flowing through the filtrate channel that is below a critical transmembrane pressure.

In some implementations, the device includes at least one pressure sensor, and the control system is configured to modify the state of the first controllable flow control device responsive to an output of the at least one pressure sensor. In some implementations, the first controllable flow control device is one of a recirculating pump, a proportional valve, a diaphragm chamber, and an outflow pump.

In some implementations, the device includes at least two controllable flow control devices configured to actively control the slope of the third pressure profile along the length of the filtrate channel relative to the slope of the second pressure profile along the length of the blood channel. In some implementations, the second controllable flow control device is configured to actively control the slope of the first pressure profile along a length of the infusate channel. The second controllable flow control device can be one of a recirculating pump, a proportional valve, a diaphragm chamber, and an influx pump.

In some implementations, the blood channel has a height in the range of about 50 µm to about 500 µm, a width in the range of about 50 µm to about 900 µm, and a length in the range of about 3 cm to about 30 cm. In some implementations, the first interchannel flow barrier is a sterility barrier.

According to another aspect of the disclosure, a microfluidic device includes a first layer defining a blood channel. The blood channel includes an inlet and an outlet and has a first pressure profile. The device also includes a second layer defining a filtrate channel that is complementary to and in fluidic communication with the filtrate channel. The filtrate channel has a second pressure profile. The device also includes a first interchannel flow barrier separating the blood channel and the filtrate channel. The first interchannel flow barrier allows a portion of a fluid flowing into the inlet of the blood channel to flow through the first interchannel flow barrier and into the filtrate channel. The device also includes a first controllable flow control device to control a difference between the first pressure profile and the second pressure profile along a length of the blood channel. The device also includes a control system that is configured to modify a state of the first controllable flow control device to set the difference between the first pressure profile and the second pressure profile.

In some implementations, setting the difference between the first pressure profile and the second pressure profile includes modifying the state of the first controllable flow control device such that the difference is greater than or less than a critical transmembrane pressure. In some implementations, setting the difference between the first pressure profile and the second pressure profile includes modifying the state of the first controllable flow control device such that the difference is greater toward the outlet of the blood channel than toward the inlet of the blood channel.

In some implementations, the blood channel has a height in a range of about 50 µm to about 500 µm, a width in the range of about 50 µm to about 900 µm, and a length in the range of about 3 cm to about 30 cm.

In some implementations, the device includes a second controllable flow control device to control the difference between the first pressure profile and the second pressure profile along the length of the blood channel. In some implementations, the first and second controllable flow control devices are one of a recirculating pump, a proportional valve, a diaphragm chamber, and an outflow pump. The device can also include at least one sensor in the filtrate channel and the blood channel.

According to another aspect of the disclosure, a method includes introducing a first fluid into a first inlet of an infusate channel defined in a first layer and having a first pressure profile. The method also includes introducing blood into a second inlet of a blood channel that is complementary to and in fluidic communication with the infusate channel. The blood channel has a second pressure profile and is defined in a second layer. The method also includes introducing a second fluid into a third inlet of a filtrate channel that is complementary to and in fluidic communication with the blood channel. The blood channel is defined in a third layer and has a third pressure profile. The method also includes setting, by a control system with a first controllable flow control device, a first slope of the third pressure profile along a length of the filtrate channel relative to the slope of the second pressure profile along the length of the blood channel. The method also includes setting, by the control system with the first controllable flow control device, a second slope of the third pressure profile along the length of the filtrate channel relative to the slope of the second pressure profile along the length of the blood channel.

In some implementations, setting the second slope of the third pressure profile includes modifying, by the control system, a state of the first controllable flow control device such that the second slope of the third pressure profile is greater than the slope of the second pressure profile. In some implementations, setting the second slope of the third pressure profile includes modifying, by the control system, the state of the first controllable flow control device such that the second slope of the third pressure profile is less than the slope of the second pressure profile. In some implementations, setting the second slope of the third pressure profile includes modifying, by the control system, the state of the first controllable flow control device such that the slope of the third pressure profile is substantially parallel to the slope of the second pressure profile. In some implementations, the method includes modifying, by the control system, a state of the first controllable flow control device to maintain a pressure difference between a pressure of the blood and a pressure of the second fluid is below a critical transmembrane pressure.

In some implementations, the method includes modifying, by the control system, the state of the first controllable flow control device to maintain a pressure difference along a length of the blood channel and the filtrate channel that does not vary by more than 50% of an average pressure difference between the blood channel and the filtrate channel.

In some implementations, the method includes setting, by the control system with a second controllable flow control device, the first slope of the third pressure profile along the length of the filtrate channel relative to the slope of the second pressure profile along the length of the blood channel. The method also includes setting, by the control system with the second controllable flow control device, the second slope of the third pressure profile.

In some implementations, the method includes receiving, by the control system from at least one pressure sensor, at least one pressure reading. The second slope of the third pressure profile is then set responsive to the at least one pressure reading. In some implementations, the first controllable flow control device is one of a recirculating pump, a proportional valve, a diaphragm chamber, and an outflow pump.

In some implementations, the blood channel has a height in a range of about 50 µm to about 500 µm, a width in the range of about 50 µm to about 900 µm, and a length in the range of about 3 cm to about 30 cm.

According to another aspect of the disclosure, a method includes introducing blood into a first inlet of a blood channel. The blood has a first pressure profile. The method also includes introducing a fluid into a second inlet of a filtrate channel that is complementary to and in fluidic communication with the blood channel. The fluid has a second pressure profile. The method also includes controlling, by a control system, a state of a first controllable flow control device to set a first difference between the second pressure profile along a length of the filtrate channel and the first pressure profile along a length of the blood channel. The method also includes modifying, by a control system, the state of the first controllable flow control device to set a second difference between the second pressure profile along the length of the filtrate channel and the first pressure profile along the length of the blood channel.

In some implementations, the second difference is less than a critical transmembrane pressure. In some implementations, the blood channel has a height in a range of about 50 µm to about 500 µm, a width in the range of about 50 µm to about 900 µm, and a length in the range of about 3 cm to about 30 cm.

The method can also include controlling, by the control system, a state of a second controllable flow control device to set the first difference between the second pressure profile along the length of the filtrate channel and the first pressure profile along the length of the blood channel. The method can also include modifying, by the control system, the state of the second controllable flow control device to set the second difference between the second pressure profile along the length of the filtrate channel and the first pressure profile along a length of the blood channel.

In some implementations, the first controllable flow control device is one of a recirculating pump, a proportional valve, a diaphragm chamber, and an outflow pump. The method can also include receiving, by the control system from at least one pressure sensor, at least one pressure reading, and then setting a state of the first controllable flow control device responsive to the received at least one pressure reading.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing.

FIGS. 2A-2H depict the device of FIG. 1C at various points in the manufacturing process, according to an illustrative implementation.

DETAILED DESCRIPTION

Following below are more detailed descriptions of various concepts related to, and implementations of, a device for increasing convective transport of solutes in blood within a dialysis system. The various concepts introduced above and discussed in greater detail below may be implemented in any of numerous ways, as the described concepts are not limited to any particular manner of implementation. Examples of specific implementations and applications are provided primarily for illustrative purposes.

Figure 1A:
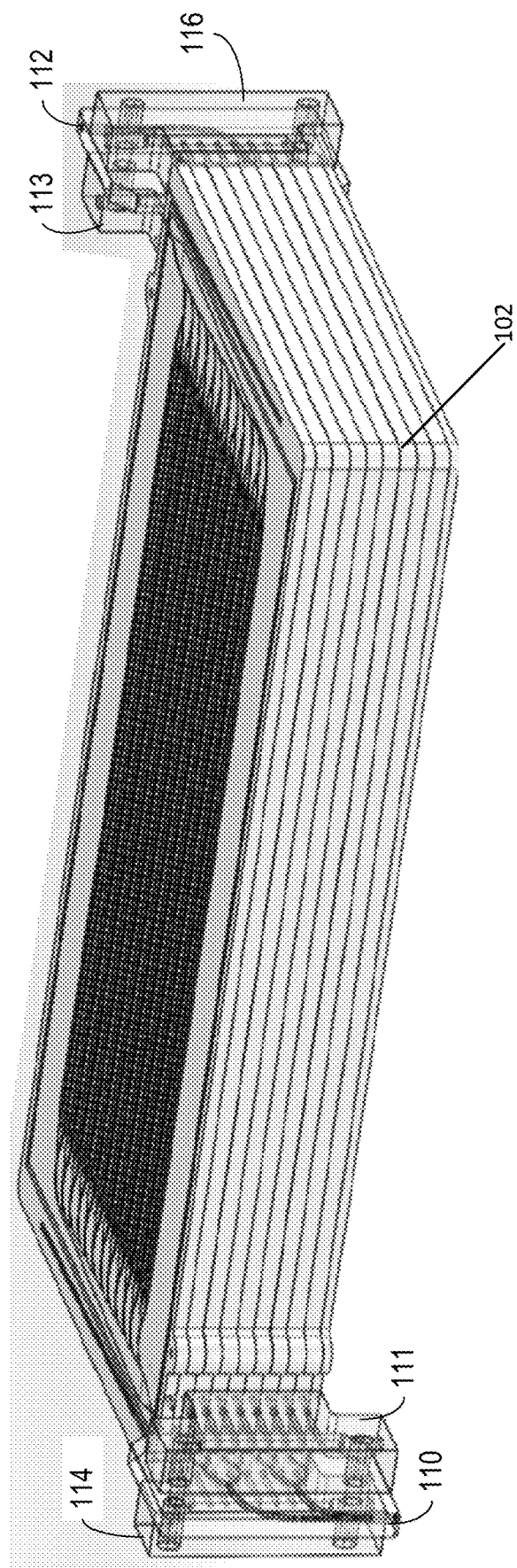
FIG. 1A illustrates a perspective view of an example microfluidic convective clearance device.

FIG. 1A is a depiction of a microfluidic convective clearance device 100. The device 100 is composed of eight layers 102. In some implementations, each layer 102 includes 96 channels, with each channel configured to provide convective therapy. In some implementations, the microfluidic convective clearance device 100, by varying the number of channels per layer or the number of layers, can include between 80 and 7000 channels to match the size of the patient, the duration of therapy, and the desired clearance dosage. Each layer 102 includes a infusate substrate, a blood flow substrate, and a filtrate substrate. The channels within each substrate are separated from the channels in different substrates by permeable membranes (also referred to as interchannel flow barriers). In other implementations, channels of a first substrate are separated from channels of a second substrate by a wall of one of the substrates (another form of interchannel flow barrier), with fluid flowing between the channels through apertures that pass through the wall separating the channels. The microfluidic convective clearance device 100 also includes a blood inlet manifold 110 and a blood outlet manifold 112, both coupled to the blood channels for the introduction and removal of blood from the device 100. A filtrate inlet manifold 114 and a filtrate outlet manifold 116 are coupled to the filtrate channels for the introduction and removal of filtrate from the device 100. The microfluidic convective clearance device 100 also includes an infusate inlet manifold 111 and an infusate outlet manifold 113 for the introduction and removal of infusate from the device. In some implementations, the channels within the blood inlet and outlet manifolds are arranged in a trunk and branch configuration. In a trunk and branch configuration a primary trunk branches multiples times into smaller branches. In some implementations, the branching in the manifolds mimics characteristics of branching in the vasculature of the body, for example, following Murray's law and including relatively smooth transitions between channels to protect blood health.

Example configurations for the layer 102 of the device 100 are described below in relation to FIGS. 1C-1E. As an overview, each layer 102 is parallel to each other layer 102. Each substrate in a layer has a thickness in the range of about 10 microns to about 10 millimeters, and the membrane 108 has thickness in the range of about 500 nanometers to about 1 millimeter. In some implementations, adjacent layers 102 can be in contact with one another. In other implementations, the layers 102 can be separated by a distance of about 500 microns or more, as illustrated in FIG. 1A.

The substrates of each layer can be made of a thermoplastic, such as polystyrene, polycarbonate, polyimide, or cyclic olefin copolymer (COC), biodegradable polyesters, such as polycaprolactone (PCL), or soft elastomers such as polyglycerol sebacate (PGS). The substrate layers may alternatively be made of polydimethylsiloxane (PDMS), poly(N-isopropylacrylamide), or nanotubes or nanowires formed from, for example, carbon or zinc oxide. In some implementations, the substrates are made of an insulating material to maintain temperature stability. In some implementations, the channels can be coated with cytophilic or cytophobic materials to promote or prevent the growth of cells, such as vascular endothelial cells, in the channels. The channels in the blood substrate layer 104 may also be coated with an anticoagulant to help prevent clotting of the blood in the blood substrate layer 104.

Figure 1B:
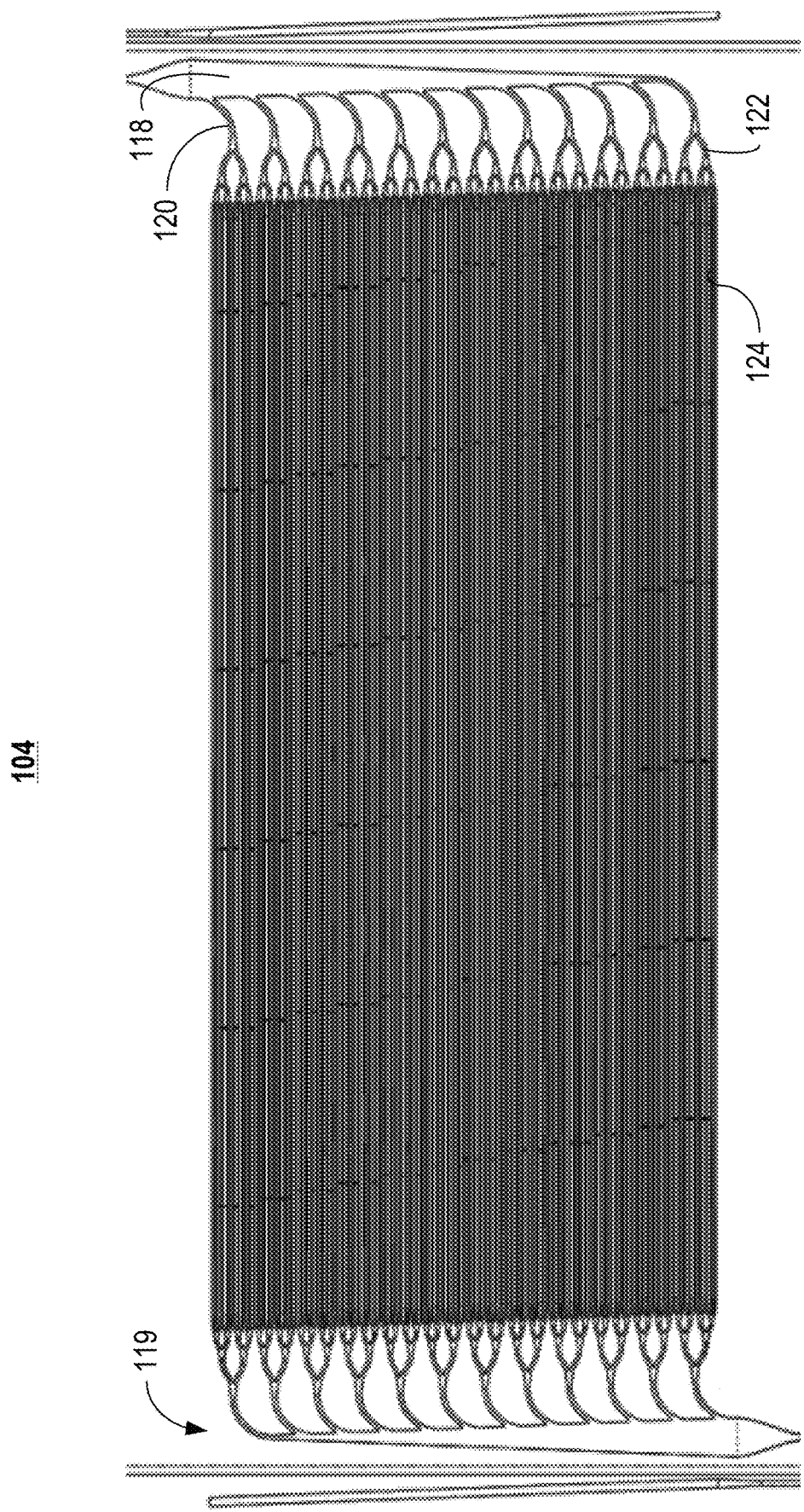
FIG. 1B illustrates an example blood substrate layer suitable for use in the microfluidic convective clearance device of FIG. 1A.

FIG. 1B illustrates an example blood substrate layer 104 suitable for use in the microfluidic convective clearance device of FIG. 1A. The blood substrate layer 104 allows blood to be distributed across a relatively large surface area within the device 100. The network of channels includes multiple blood channels 126. Blood is supplied and removed from the blood channels through biomimetic branching structures 119. Each branching structure 119 includes a primary channel 118, a plurality of secondary channels 120, and a plurality of tertiary channels 122. In some implementations, the blood channels 126 have a height in the range of about 50 µm to about 500 µm, a width in the range of about 50 µm to about 900 µm, and a length in the range of about 3 cm to about 30 cm or about 15 cm to about 25 cm.

Figure 1C:
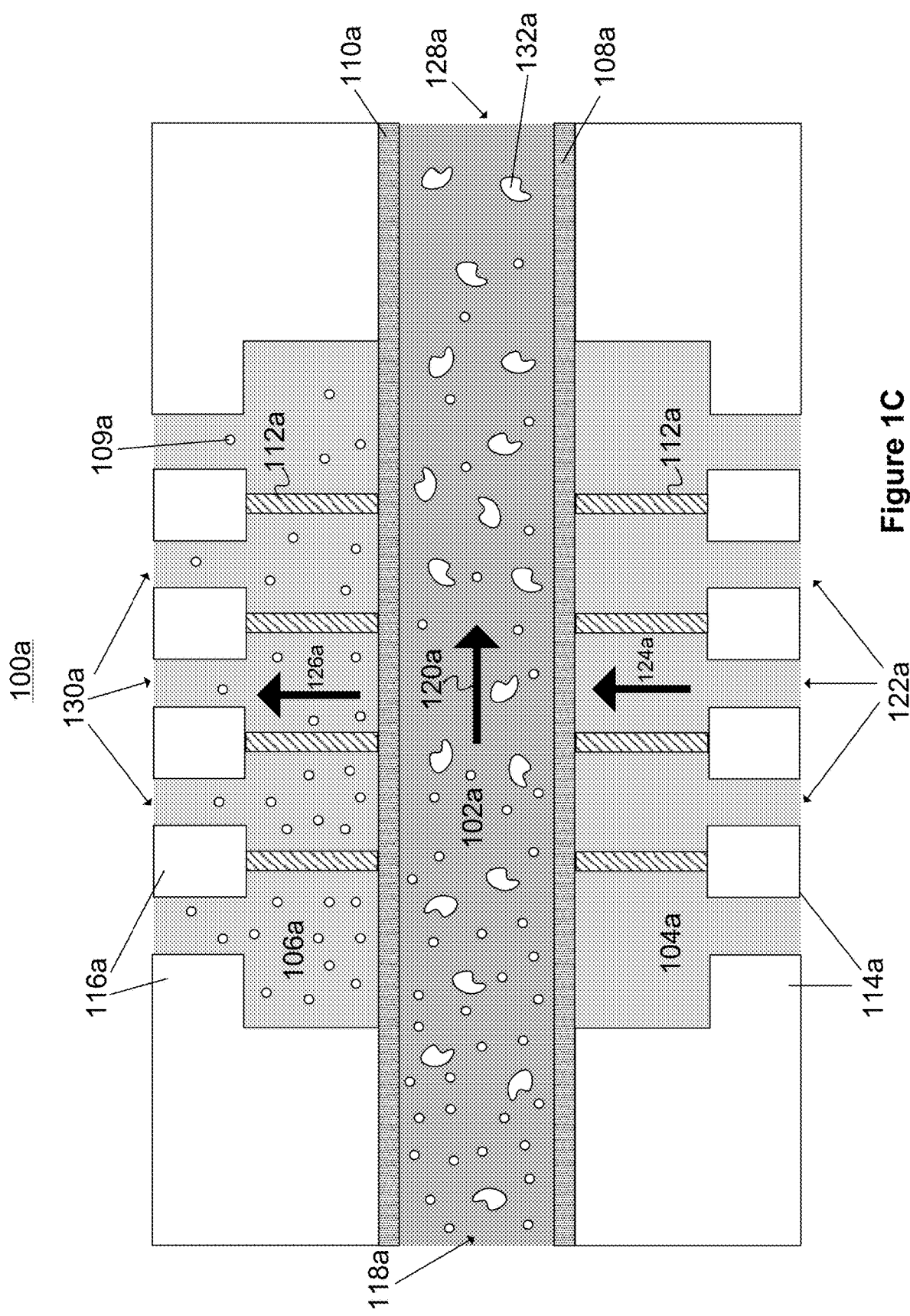
FIG. 1C illustrates a cross-sectional view of a first microfluidic convective clearance device layer for use in hemofiltration device illustrated in FIG. 1A.

FIG. 1C is a cross-sectional view of a first microfluidic convective clearance device layer 100a for use in hemofiltration system such as that illustrated in FIG. 1A. The convective clearance device layer 100a includes a blood channel 102a, an infusate channel 104a, and a waste channel 106a (also referred to as a "filtrate channel"). A first membrane 108a separates the blood channel 102a from the infusate channel 104a, and a second membrane 110a separates the blood channel 102a from the waste channel 106a. The infusate channel 104a and the waste channel 106a also include structural supports 112a.

The blood channel 102a has a depth in the range of about 50 microns to about 500 microns, a width in the range of about 50 microns to about 900 microns, and a length in the range of about 3 centimeters to about 20 centimeters. The infusate channel 104a is defined by an infusate substrate 114a and the waste channel 106a is defined by a waste substrate 116a (also referred to as a "filtrate substrate"). The substrates 114a and 116a can be made from a polystyrene, polycarbonate, polyimide, polysulfone, polyethersulfone, acrylic, or cyclic olefin copolymer (COC), biodegradable polyesters, such as polycaprolactone (PCL), soft elastomers such as polyglycerol sebacate (PGS), or other thermoplastics. The substrates may alternatively be made of polydimethylsiloxane (PDMS), poly(N-isopropylacrylamide), or nanotubes or nanowires formed from, for example, carbon or zinc oxide.

The upper and lower walls of the blood channel 102a are defined by the membranes 110a and 108a, respectively. In some implementations, the side walls of the blood channel can be made from a substrate material similar to the substrates 114a and 116a. The blood channel 102a can be coated with cytophilic or cytophobic materials to promote or prevent the growth of cells, such as vascular endothelial cells, in the channels. The blood channel 102a may also be coated with an anticoagulant to help prevent clotting of the blood. In some implementations, the anticoagulant is applied to the substrate walls of the blood channel 102a, but not to the walls defined by the membranes 108a and 110a.

The convective clearance device layer 100a is designed for use in hemofiltration. The blood channel 102a, the infusate channel 104a, and the waste channel 106a are configured such that a relatively large surface area of the fluid flowing through the channels is exposed to the membranes 108a and 110a. In some implementations, the channels 102a, 104a, and 106a can have rectangular cross-sections, with a relatively large fluid interface at the membranes 108a and 110a, to promote fluid communication between the blood channel 102a, the infusate channel 104a, and the waste channel 106a. The channels 102a, 104a, and 106a can alternatively have semicircular cross sections. In other implementations, the channels 102a, 104a, and 106a may have any other type of cross section, such as a substantially rectangular cross-section with rounded corners, or an irregularly shaped cross-section.

Blood is introduced into an inlet 118a of the blood channel 102a and flows along the length of the blood channel 102a in the direction indicated by arrow 120a. Infusate (e.g., saline or physiologically balanced replacement solution) is simultaneously introduced into the infusate channel 104a through inlets 122a. A transverse pressure is applied to the infusate channel 104a and the waste channel 106a, causing fluid in these channels to flow in the directions indicated by the arrows 124a and 126a, respectively. As blood flows through the blood channel 102a, the transverse pressure gradient causes an infusion of infusate to flow from the infusate channel 104a, through the membrane 108a, and into the blood channel 102a. The transverse pressure causes fluid from the blood channel 102a, including plasma, urea, and other waste particles, such as particle 109a, to be forced into the waste channel 106a through the membrane 110a. Cleansed blood can then be collected from an outlet 128a of the blood channel 102a. In some implementations, waste-collecting fluid passes out of the convective clearance device layer 100a through outlets 130a in the waste collecting channel, and can then be filtered and recirculated back to the inlets 122a of the infusate channel 104a. Blood and infusate can be introduced in such a way as to maintain substantially laminar flow in the blood channel 102a. In some implementations, the infusate channel 104a and the waste channel 106a can be reservoirs or fluid baths whose volume is significantly larger than the volume of the blood channel 102a. In some implementations, a dialysate can be introduced to chamber 106a to allow diffusive transport in addition to the convective transport due to flow 126a.

The membrane 110a can be configured to allow clearance of particles having a molecular weight of less than about 60 kDa. Larger particles exemplified by particle 132a, such as blood cells, can remain within the blood channel. The membrane 108a can be identical to the membrane 110a. However, in some implementations, the membrane 108a can have pore sizes that are significantly smaller than the pore sizes of the membrane 110a, because it is only necessary to allow fresh infusate to pass through the membrane 108a. For example, smaller pore sizes may be selected to prevent the introduction of impurities into the blood channel 102a while still allowing infusate to flow into the blood channel 102a. For example, a pore size less than about 0.2 µm can reduce (or substantially prevent) the passage of bacteria across the membrane 108a. In other implementations, desirable solutes may be introduced into the infusate channel 104a, and the membrane 108a can be configured to allow the desirable solutes to pass into the blood channel 102a. The membrane 108a can be made from an impermeable material into which pores have been fashioned, for example by a laser etching process. Alternatively, the membrane 108a can be constructed from a naturally porous material.

The pressure gradient indicated by the arrows 124a and 126a is substantially constant throughout the lengths of the infusate channel 104a and the waste channel 106a. For example, substantially constant pressure can be achieved by positioning a number of inlets 122a along the length of the infusate channel 104a. Similarly, a number of outlets 130a can be positioned along the length of the waste-collecting channel 106a. This allows the blood channel 102a to experience a simultaneous infusion of fluid from the infusate channel 104a and outflow of fluid to the waste channel 106a, which results in a substantially constant volume of blood along the length of the blood channel 102a. By contrast, in typical hemodialysis devices, forward filtration occurs along a portion of the length of the device, and back filtration occurs along a separate portion of the device, resulting in a varying fluid volume profile along the length of the device. Achieving increased convective clearance in these types of devices requires a larger variance of the volume of blood along the length of the device, which can lead to unsafe hematocrit levels.

Hematocrit in the blood channel 102a is preferably maintained within an acceptable range in order to ensure blood health. The substantially constant volume of fluid maintained in the blood channel 102a causes a substantially constant hematocrit level in the blood channel 102a. Therefore, the amount of convective clearance achieved in the convective clearance device layer 100a can be increased without significantly increasing the risk of unsafe hematocrit levels. In some implementations, the amount of convective clearance is proportional to the magnitude of the transverse pressure gradient indicated by arrows 124a and 126a. As discussed above, increasing the infusion of fluid from the infusate channel 104a to the blood channel 102a allows increased outflow of fluid from the blood channel 102a to the waste channel 106a, while preserving the volume of fluid in the blood channel 102a. Other hemodialysis devices typically require increased channel lengths, increased blood flow, and increased residence time of fluid in the channels in order to increase the amount of convective clearance. The convective clearance device layer 100a can therefore be used to achieve significantly higher levels of convective clearance without a need for increasing the overall size of the convective clearance device layer 100a.

The transverse pressure gradient may expose the membranes 108a and 110a to stresses that can cause the membrane 108a to deform towards the blood channel 102a and can cause the membrane 110a to deform towards the waste channel 106a. To prevent significant deformation of the membranes 108a and 110a, the infusate channel 104a and the waste-collecting channel 106a can include structural supports 112a. The structural supports 112a can span the width of the infusate channel 104a and the waste-collecting channel 106a, and can be attached to the membranes 108a and 110a to hold them in place against the force of the fluid pressure gradient indicated by arrows 124a and 126a. In other implementations, the structural supports 112a can substantially fill the volume of the infusate channel 104a and the waste channel 106a to provide rigidity to the channels 104a and 106a and reduce deformation of the membranes 108a and 110a. For example, the structural supports 112a can be porous mesh structures made from ceramic, carbon, polymer, or other materials. The structural supports 112a can also be posts or ridges inserted into the blood channel 102a, the infusate channel 104a, or the waste-collecting channel 106a. To prevent the obstruction of fluid flow in the infusate channel 104a and the waste-collecting channel 106a, the structural supports 112a can be selected to have pore sizes that are larger than the pore sizes of the membranes 108a and 110a, so that the clearance of particles from the fluids is controlled only by the pore sizes of the membranes 108a and 110a.

In some implementations, a microfluidic convective clearance device similar to the device layer 100a can be configured such that only a portion of the fluid in the infusate channel and waste channel flows perpendicular to the flow of fluid in the blood channel, while the remaining portion of fluid in the infusate channel and waste channel flows parallel to the flow of fluid in the blood channel. An example of such a device is shown in FIG. 1D FIG. 1D is a cross-sectional view of a second microfluidic convective clearance device 100b for use in hemofiltration, according to an illustrative implementation. The device 100b includes many of the features of the device layer 100a shown in FIG. 1C. For example, the device 100b includes a blood channel 102b, an infusate channel 104b, and a waste-collecting channel 106b. The channels are defined by walls made from substrate materials 114b and 116b and membranes 108b and 110b, and can include structural supports 112b. Fluid can be introduced into an inlet 140b of the infusate channel 104b. The pressure in the infusate channel 104b causes some of the fluid to pass through the membrane 108b and into the blood channel 102b, in the direction shown by the arrow 127b. The remaining portion of the fluid in the infusate channel 104b can travel parallel to the blood channel 102b along the length of the channel 104b, as shown by the arrow 125b, and can be collected at an outlet 142b.

Undesired particles, such as particle 109b, can also pass through the membrane 110b into the waste-collecting channel 106b. In some implementations, additional waste-collecting fluid can be introduced at an inlet 146b of the waste-collecting channel 106b, causing fluid within the waste-collecting channel 106b to flow in the direction shown by arrow 131B. Waste-collecting fluid can be collected from the outlet 144b, and purified blood can be collected from the outlet 128b as the blood flows along the blood channel 102b in the direction shown by the arrow 120b. In some other implementations, the waste-collecting fluid can be introduced such that the fluid in the waste-collecting channel flows in a direction opposite the direction shown by arrow 131C. In some implementations, the waste collecting fluid introduced can be a dialysate to provide diffusive clearance in addition to convective clearance.

Figure 1D:
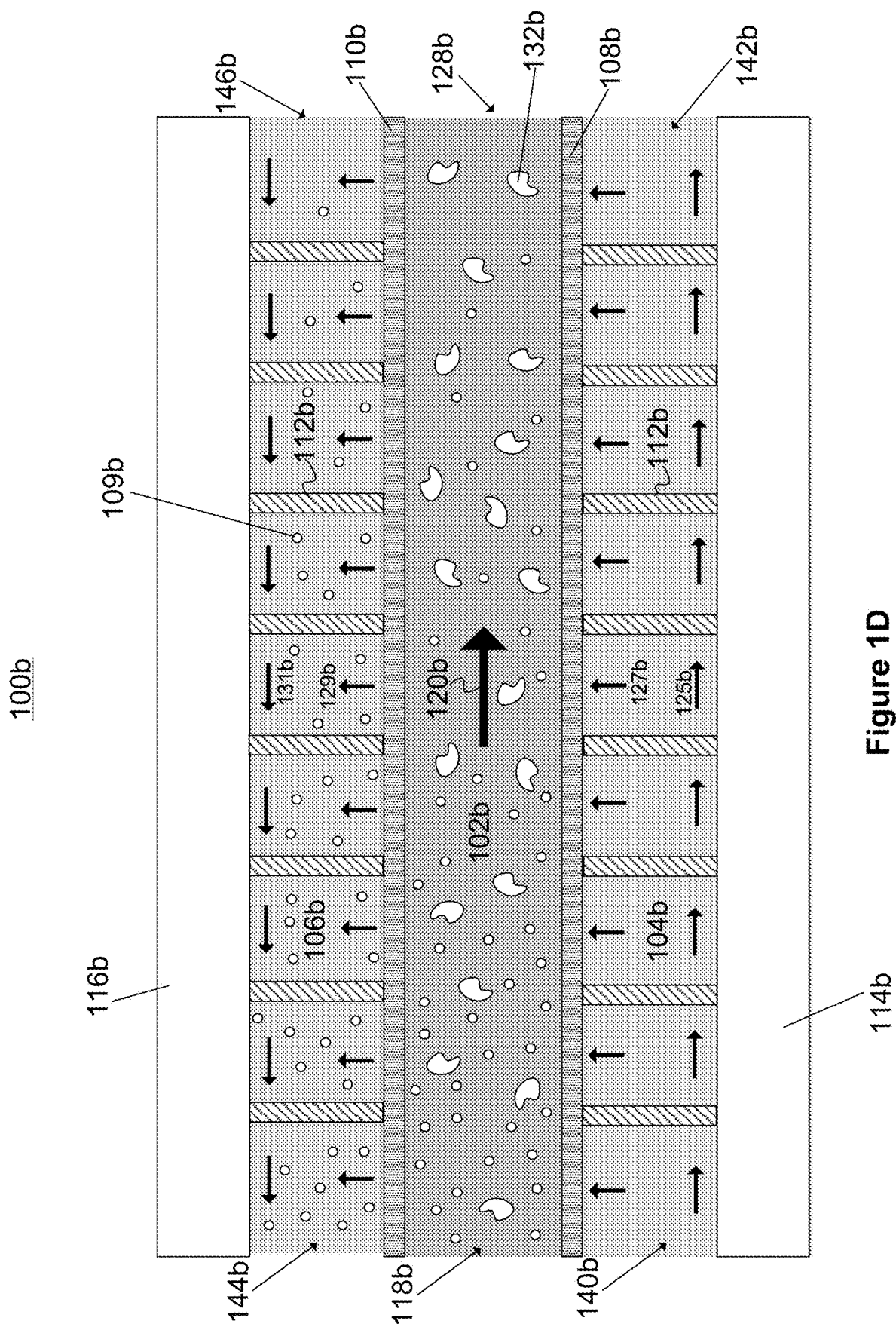
FIG. 1D illustrates a cross-sectional view of a second microfluidic convective clearance device layer for use in hemofiltration device illustrated in FIG. 1A.
Figure 1E:
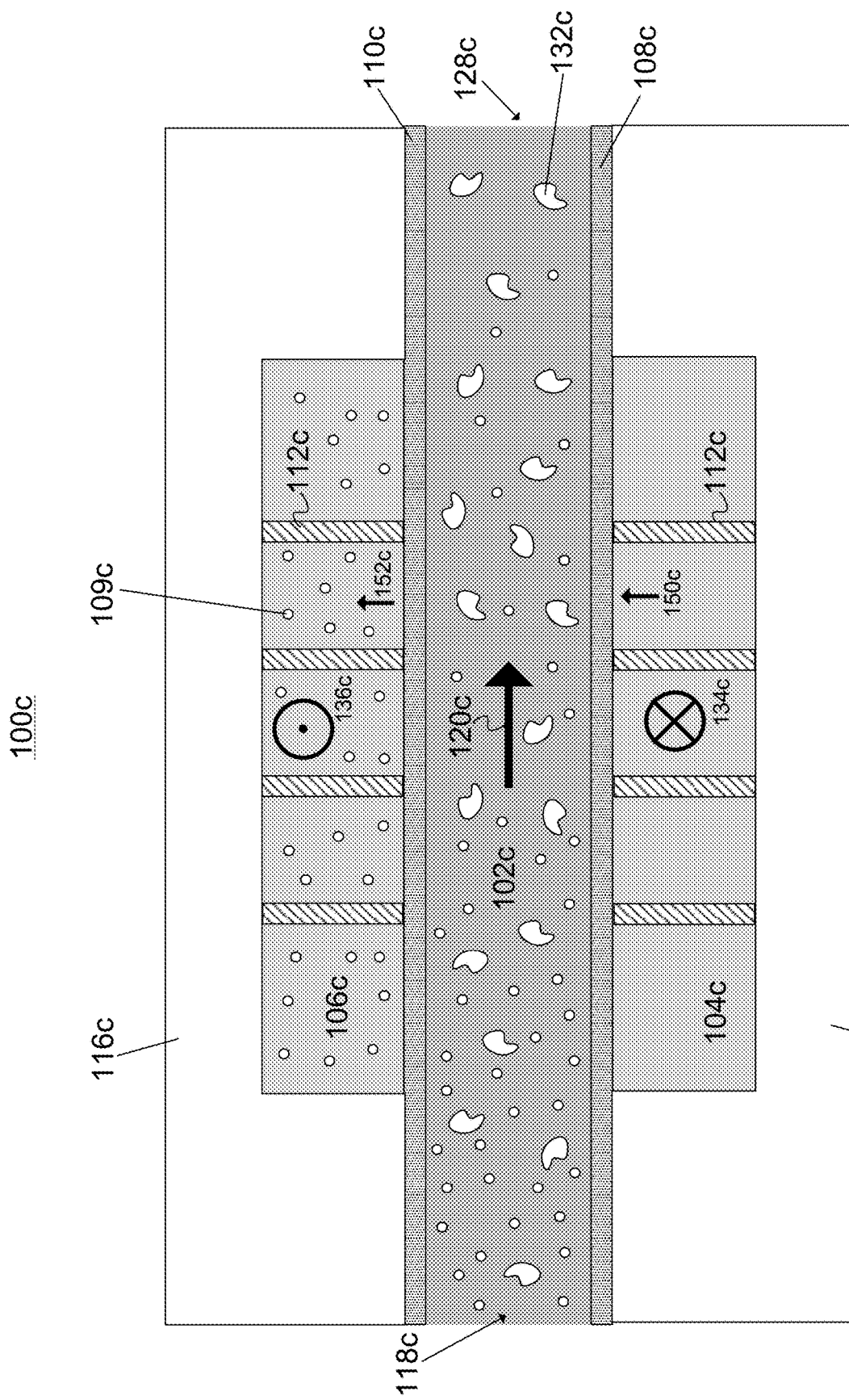
FIG. 1E illustrates a cross-sectional view of a third microfluidic convective clearance device layer for use in hemofiltration device illustrated in FIG. 1A.

FIG. 1E is a cross-sectional view of a third microfluidic convective clearance device 100c for use in hemofiltration, according to an illustrative implementation. The device 100c includes many of the features of the device layer 100a shown in FIG. 1C. For example, the device 100c includes a blood channel 102c, an infusate channel 104c, and a waste-collecting channel 106c. The channels are defined by walls made from substrate materials 114c and 116c and membranes 108c and 110c, and can include structural supports 112c. Unlike the device 100b of FIG. 1D in which the an infusate channel 104b and a waste collecting channel 106b run parallel to the blood channel 102b, the infusate channel 104c and waste-collecting channel 106c of the device 100c are oriented perpendicular to the blood channel 102c.

Fluid can be introduced into an inlet of the infusate channel 104c in the direction shown by the vector 134c (e.g., directed into the page). The pressure in the infusate channel 104c causes some of the fluid to pass through the membrane 108c and into the blood channel 102c, in the direction shown by the arrow 150c. The remaining portion of the fluid in the infusate channel 104c can travel along the length of the channel 104c, in the direction of the vector 134c, and can be collected at an outlet.

Higher pressure is maintained in the blood channel 102c as compared to the waste-collecting channel 106c, causing some of the fluid in the blood channel 102c to pass into the waste-collecting channel 106c through the membrane 110c, in the direction shown by the arrow 152c. Undesired particles, such as particle 109c, can also pass through the membrane 110c into the waste-collecting channel 106c. In some implementations, additional waste-collecting fluid can be introduced at an inlet of the waste-collecting channel 106c, causing fluid within the waste-collecting channel 106c to flow in the direction shown by vector 136c (e.g., out of the page). Waste-collecting fluid can be collected from an outlet of the waste-collecting channel, and purified blood can be collected from the outlet 128c of the blood channel 102c as the blood travels along the blood channel 102c in the direction shown by arrow 120c. In some other implementations, the waste-collecting fluid can be introduced such that the fluid in the waste-collecting channel flows in a direction opposite the direction shown by vector 136c (e.g., parallel to the direction of fluid flow in the infusate channel 104c. In some implementations, the waste collecting fluid introduced can be a dialysate to provide diffusive clearance in addition to convective clearance.

FIGS. 2A-2F depict the device of FIG. 1C at various points in the manufacturing process. FIG. 2A shows a rectangular block of substrate material 216. The substrate material can be used to form either the infusate channel or the waste-collecting channel of FIG. 1C, as both of these channels are very similar. Therefore, the processes discussed in connection with the manufacture of either channel will also be useful in the manufacture of the other. The substrate material 216 can be any of the materials described above in connection with the substrates used in the device of FIG. 1C, such as thermoplastics, biodegradable polyesters, or nanotubes or nanowires formed from, for example, carbon or zinc oxide. The substrate material 216 can be a solid block whose dimensions are selected to provide sufficient volume to form the infusate channel or waste collecting channel of FIG. 1C.

FIG. 2B shows a cross-sectional view of the substrate 216 of FIG. 2A after it has been hollowed out to form a channel 206. For example, the channel 206 can be used as the infusate channel or the waste-collecting channel of FIG. 1C. The channel 206 can be created in the substrate 216 by any method of material removal, such as an etching or milling process. The result is the hollow channel 206 suitable for carrying infusate or waste-collecting fluid, surrounded on three sides by the substrate material 216. The fourth side of the channel will be formed by a membrane, so the substrate material 216 is completely removed from this side.

FIG. 2C shows a cross-sectional view of the substrate 216 and the channel 206. Also shown are openings 230 leading into the channel 206. The openings 230 can be used as the infusate inlets or waste fluid outlets described in FIG. 1C. In some implementations, the openings 230 are positioned evenly across the surface of the substrate 216, to facilitate an even pressure gradient along the length of the channel 206. Although five openings 230 are shown in FIG. 2C, any number of openings 230 can be present. In some implementations, the openings can be created by a chemical or laser etching, drilling, or milling process in which material is removed from the surface of the substrate 216. The shape of the openings can be circular, rectangular, or any other shape suitable for introducing fluid into the openings (e.g., into the inlets of the infusate channel of FIG. 1C) or extracting fluid from the openings (e.g., from the outlets of the waste-collecting channel of FIG. 1C).

FIG. 2D shows a cross-sectional view of the substrate material 216, channel 206, and openings 230. Also shown in FIG. 2D are structural supports 212 coupled to the substrate 216. The structural supports 212 are intended to reinforce the structural integrity of the channel 206 and to prevent deformation of a membrane that will be added later in the process, so the structural supports 212 are preferably made from a substantially rigid material such as a polymer or a metal. As shown in FIG. 2D, the structural supports can be aligned with the direction of fluid flow in the channel 206 (see arrows 124a and 126a of FIG. 1C), in order to reduce interference with the flow of infusate or waste-collecting fluid in the channel 206. In other implementations, the structural supports 212 can occupy a substantial portion of the channel 206. For example, the structural supports 212 can be made from a porous material that allows fluid to flow through the channel 206. The structural supports 212 can be coupled to the substrate 216 by a mechanical joint or by a medical grade adhesive suitable for use in a fluid channel.

FIG. 2E shows a cross-sectional view of the substrate 216 configured as in FIG. 2D, with the addition of a membrane 210. The membrane 210 can be used as either of the membranes 108a or 110a of FIG. 1C. In some implementations, the membrane 210 is selected to allow clearance of particles having a molecular weight smaller than about 60 kDa. The membrane 210 is coupled to the structural supports 210 in order to prevent the membrane 210 from deforming under the pressure of the fluid flowing through the channel 206. The membrane 210 can be joined to the structural supports 212 by a mechanical fastener or by an adhesive.

FIG. 2F shows the features of the infusate channel of FIG. 1C. As discussed above, the elements shown in FIG. 2E can be used to form either the infusate channel or the waste-collecting channel of FIG. 1C. Therefore, structure of FIG. 2F can be manufactured by repeating the process described in connection with FIGS. 2A-2E to produce a second structure. The structure of FIG. 2F is similar to the structure shown in FIG. 2E, but rotated 180 degrees such that the openings 230 of FIG. 2F are opposed to the openings of FIG. 2E.

Figure 2G:
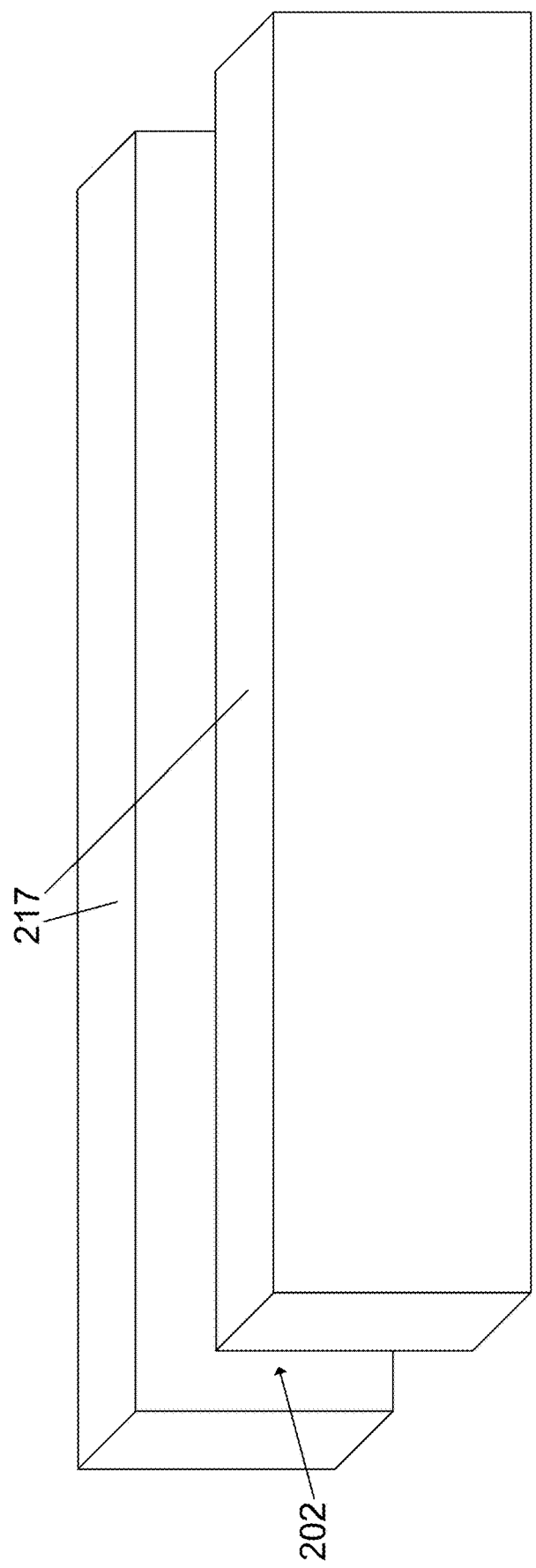

FIG. 2G shows a pair of substrate walls 217. The substrate walls are parallel to each other and define the side walls of a channel 202, which can be used as the blood channel of FIG. 1C. The channel 202 is open on its top and bottom sides at this step in the process, but will eventually be defined by the membranes 210 as shown in FIG. 2H.

Figure 2H:
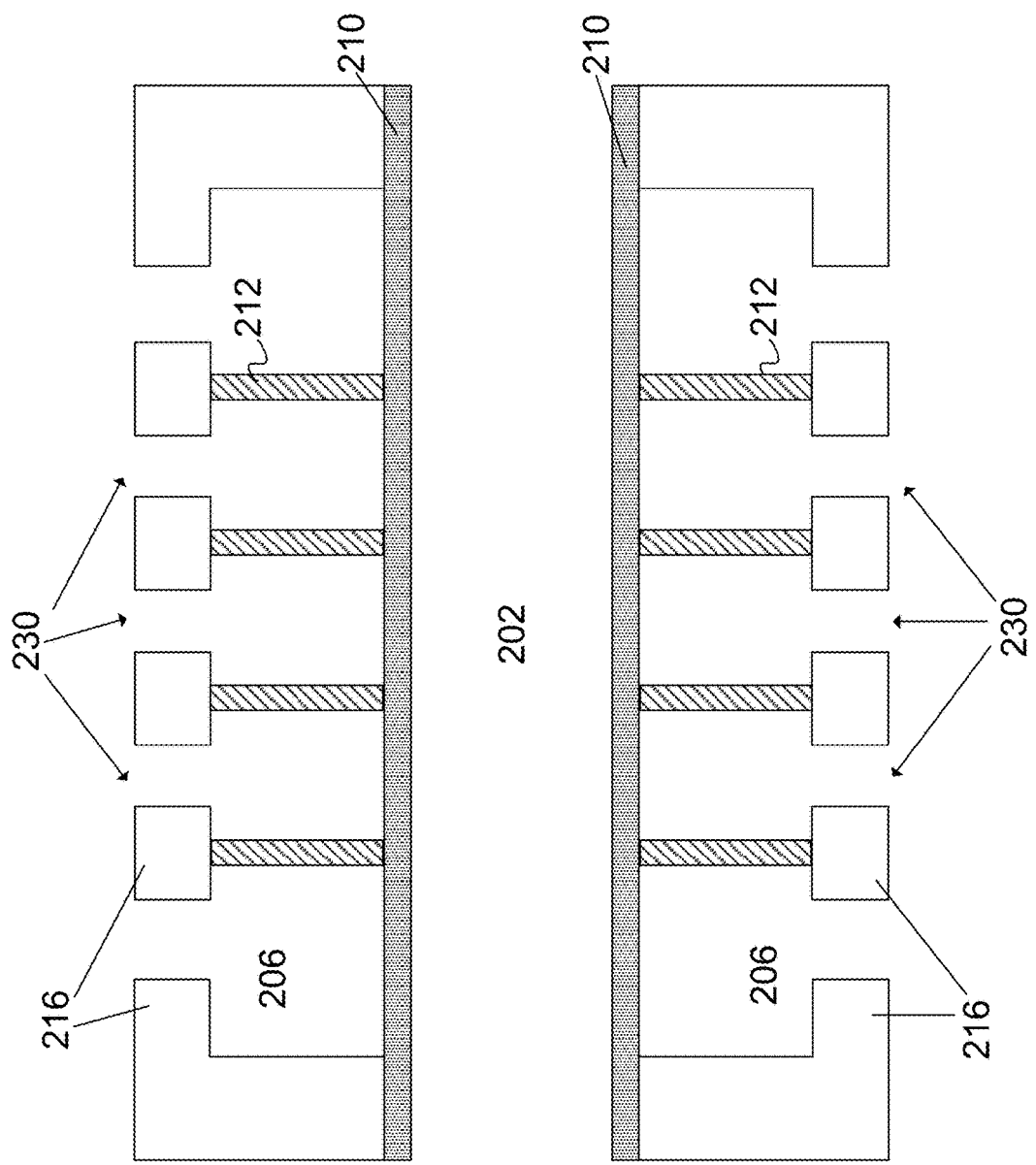

FIG. 2H shows the final step of the manufacturing process for manufacturing the device of FIG. 1C. The membranes 210 of the two instances of channel 206 (depicted in FIGS. 2E and 2F) are joined to the substrate walls 217 (depicted in FIG. 2G) to form the channel 202, which is defined on its upper and lower walls by the membranes 210, and on its sides by the substrate walls 217 as shown in FIG. 2G. The substrate walls 217 are not visible in the cross-sectional view of FIG. 2H. The channel 202 can be used as the blood channel of FIG. 1C, while the channels 206 can be used as the infusate channel and waste-collecting channel. In other implementations, the manufacturing process can include a net shape molding process.

Figure 3:
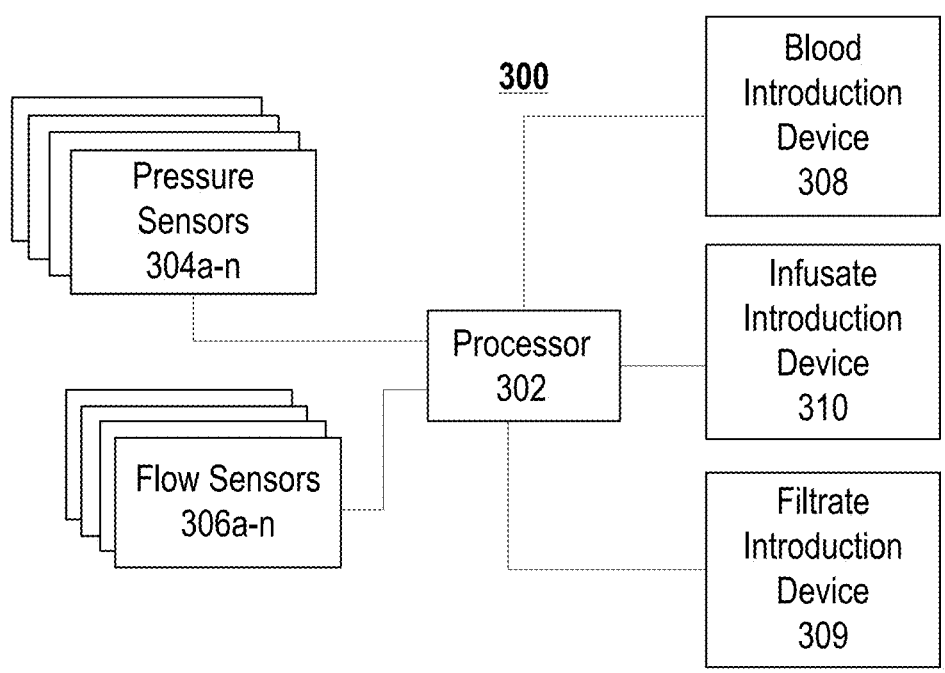
FIG. 3 illustrates an example block diagram of a control system that can be used with the devices of FIG. 1A, according to an illustrative implementation.

FIG. 3 depicts a block diagram of a control system 300 that can be used with the devices of FIGS. 1C-1E. The control system 300 includes an electronic processor 302 in communication with fluid pressure sensors 304, fluid flow sensors 306, a blood introduction device 308, a filtrate introduction device 309 and an infusate introduction device 310. Because the devices of FIGS. 1C-1E are intended for use in hemofiltration, promoting health of the patient's blood as it flows through the blood channel is important. The control system 300 can be used to ensure that the patient's blood remains healthy.

Pressure sensors 304 and flow sensors 306 can be placed inside the blood channel. In some implementations, the physical shape of the fluid pressure sensors 304 and the flow sensors 306 can be selected to reduce interference with the flow of blood in the blood channel. For example, the pressure sensors 304 and the flow sensors 306 can have a small size or a hydrodynamic shape in order to promote laminar fluid flow. During operation of the device, the pressure sensors 304 and the flow sensors 306 can measure the pressure and flow characteristics in the blood channel and can transmit the measurements to the processor 302. The pressure sensors 304 and the flow sensors 306 can report measurements continuously, or at predetermined time intervals.

The processor 302 can determine whether the pressure and flow in the blood channel are suitable for maintaining blood health. The processor 302 can compare the measurements taken by the pressure sensors 304 and the flow sensors 306 to predetermined ranges that are deemed to be safe for blood. If the pressure or flow rate is outside of the acceptable range, the processor can attempt to correct the problem by transmitting signals to the blood introduction device 308, the filtrate introduction device 309, or the infusate introduction device 310. For example, the processor can reduce the flow rate in the blood channel by triggering the blood introduction device 308 (e.g., a pump) to decrease the amount of blood introduced at the inlet of the blood channels. The processor can also respond to an unacceptably high fluid pressure in the blood channel by triggering the infusate introduction device 310 to reduce the rate at which infusate is introduced at the inlets to the infusate channel. In another example, the processor can trigger the infusate introduction device 310 to increase the rate at which infusate is introduced (e.g., to decrease the hematocrit in the blood channel). In another example, the filtrate introduction device 309 can control the pressure differential between the blood and filtrate channels by decreasing or increasing the amount of filtrate introduced at the inlet of the filtrate channels. In some implementations, the processor 302 can control the blood introduction device 308, the filtrate introduction device 309, and the infusate introduction device 310 to achieve a desired hematocrit profile in the blood channel. For example, the processor 302 can control the blood introduction device 308 and the infusate introduction device 310 to maintain a constant hematocrit level throughout the blood channel. Alternatively, in some implementations, the processor 302 can control the blood introduction device 308 and the infusate introduction device 310 to create a hematocrit profile that varies along the length of the blood channel.

Figure 4:
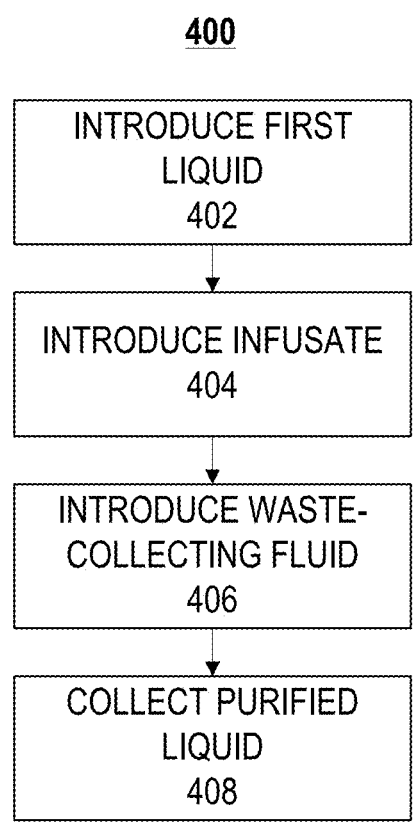
FIG. 4 illustrates a flow diagram of a method for filtering liquid containing an analyte, according to an illustrative implementation.

FIG. 4 is a flow diagram of a method 400 for filtering liquid containing an analyte, according to an illustrative implementation. The method 400 includes the steps of introducing a first liquid solution (step 402), introducing infusate (step 404), introducing waste-collecting fluid (step 406), and collecting the cleansed liquid (step 408). In step 402, a first liquid containing an analyte is introduced into an inlet of one or more first channels. In some implementations, the fluid is blood that has been extracted from a patient for filtration. The analyte can be any undesirable substance, such as urea, uric acid, creatinine, or other toxins or pathogens. The first channels can have a height in the range of about 50 microns to about 500 microns, about 100 microns to about 400 microns, or about 200 microns to about 300 microns. The first channels can have a width in the range of about 50 microns to about 900 microns, about 200 microns to about 750 microns, about 350 microns to about 600 microns, or about 350 microns to about 450 microns. The length of the first channels can be in the range of about 3 centimeters to about 25 centimeters, about 10 centimeters to about 25 centimeters, or about 15 centimeters to about 20 centimeters. In some implementations, if blood is to be introduced into the first channel, the first channel can include an anticoagulant coating on its inner walls and can be configured to maintain wall shear rates in the range of about 100 inverse seconds to about 3500 inverse seconds.

The method 400 includes the step of introducing infusate into an inlet of at least one second channel (step 404). The second channel is complementary to one or more of the first channels, and the infusate is introduced into the second channel such that it flows in a direction perpendicular to the direction of the first liquid in the first channel. The second channel is separated from the one or more complementary first channels by a first permeable membrane, which allows some of the infusate to be transported from the second channel into the first channel.

The method 400 includes the step of introducing waste-collecting fluid into an inlet of at least one third channel (step 406). The third channel is complementary to one or more of the first channels, and the third channel is separated from the one or more complementary first channels by a second permeable membrane, which allows some of the analyte to be transferred from the first channel to the third channel. In some implementations, introducing the first liquid (step 402), introducing the infusate (step 404), and introducing the waste-collecting fluid (step 406) can occur simultaneously and continuously. The waste-collecting fluid can be introduced such that the pressure in the third channel is less than the pressure in the adjacent first channel, which can result in an outflow of fluid form the first channel to the third channel. In some implementations, the waste collecting fluid introduced can be a dialysate to provide diffusive clearance in addition to convective clearance.

In some implementations, introducing the first liquid (step 402), introducing the infusate (step 404), and introducing the waste-collecting fluid (step 406) can occur simultaneously and continuously. For example, the first liquid, infusate, and waste-collecting fluid can be flowed continuously through their respective channels. Infusate is transported from the second channel to the first channel through the first membrane. The infusion of infusate into the first channel allows an outflow of fluid from the first channel to the third channel through the second membrane while maintaining a fluid balance in the first channel. Waste particles, such as urea, uric acid, or creatinine, are also transported through the second membrane and into the third channel. The waste-collecting fluid in the third channel then carries the waste particles away from the first channel.

As discussed above, the first liquid can be blood that has been extracted from a patient for cleansing. The ratio of liquid to red blood cells in the first channel can be substantially constant along its length so as to maintain substantially constant hematocrit in the blood. Blood health can also be preserved by maintaining laminar flow in the first channel and holding fluid shear rates in a range of about 100 to about 3500 inverse seconds.

The method 400 can also include the step of collecting cleansed liquid from an outlet of the one or more first channels (step 408). As the liquid is transported along the length of the first channel from the inlet to the outlet, some of the waste particles in the liquid are removed from the first channel through the second membrane, as discussed above. Therefore, when the liquid reaches the outlet of the first channel, it has a substantially smaller concentration of waste particles. If the fluid is blood that has been extracted from a patient, the filtered blood can be collected at the outlet of the first channel and can then be returned to the patient.

FIGS. 5A, 5B, 6A-10, and 13 illustrate example microfluidic convection clearance devices. Each of the devices described in relation to FIGS. 5A, 5B, 6A-10, and 13 can form a layer 102 of the device illustrated in FIG. 1A. FIG.

5A illustrates a cross-sectional view of a microfluidic convective clearance device 500 for use in hemofiltration. The device 500 includes an infusate channel 501 and a filtrate channel 502 on either side of a blood channel 503. The blood channel 503 is separated from the infusate channel 501 and from the filtrate channel 502 by a membrane 504 (also referred to as an interchannel flow barrier). The filtrate channel 502 is in fluid communication with a filtrate reservoir 506, and the infusate channel 501 is in fluid communication with an infusate reservoir 505 via manifolds such as those described above in relation to FIG. 1A. A pump 509 is placed in-line with the infusate reservoir 505 and the filtrate reservoir 506. A valve 510 is placed in-line with each of the pumps 509. The substrate defining infusate channel 501, the substrate defining filtrate channel 502, and the substrate defining blood channel 503 can form a layer 102 of the device 100 illustrated in FIG. 1A.

The fluid exiting the infusate channel 501 and the filtrate channel 502 return to the infusate reservoir 505 and the filtrate reservoir 506, respectively, and can be recycled through the device 500. The infusate reservoir 505 includes an inlet 507 where fresh infusate is added to the device 500. The filtrate reservoir 506 includes an outlet 508 where collected filtrate is removed from the device 500. In other implementations, the inlet 507 and the outlet 508 are placed at any location along their respective fluidic circuits. In some implementations, the filtrate channel 502 and the infusate channel 501 are not coupled to dedicated reservoirs. In these implementations, the tubing coupling the outlet of each channel back to the inlet of the channel functions as a fluid reservoir.

In general, the device 500 performs hemofiltration by flowing blood through the blood channel 503. Initially, the blood in the blood channel includes a plurality of particles 109, which can include urea, middle molecules, and other waste molecules to be filtered out of the blood. Infusate is flowed into the channel 501, creating a pressure gradient in the infusate channel 501. The infusate is pumped into the infusate channel 501 at a rate such that the pressure drop in the the infusate channel 501 is controlled relative to the pressure drop in the blood flow channel 503. The infusate is pumped into the infusate reservoir 505 through the inlet 507 at a rate such that the pressure at any given point along the infusate channel 501 is greater than the pressure in the blood flow channel 503, resulting in a transmembrane pressure differential. The transmembrane pressure forces fresh infusate 514 through the membrane 504, and into the blood channel 503. A pressure differential between the blood channel 503 and the filtrate channel 502 causes a flow 515 from the blood channel 503 and into the filtrate channel 502. The flow 515 carries the particles 109 through the second membrane 504 and into the filtrate channel 502. The particles 109 can be removed from the filtrate in the filtrate reservoir 506. In some implementations, the filtrate is not filtered and a portion of the filtrate is removed from an outlet of the filtrate fluid circuit to create a vacuum that helps pull the particles 109 and other fluids from the blood channel 503 into the filtrate channel 502. For example, a fluid of volume substantially equal to the amount of fluid desired to pass into the filtrate channel 502 from the blood channel 503 is removed. In some implementations, between about 5% and about 40%, about 5% and about 20%, or about 10% and about 20% of the fluid flow rate of fluid flowing through the filtrate channel 502 is removed through each cycle.

In device 500, as the blood flows down the length of the blood channel 503, the waste particles 109 are removed from the blood. The blood is reinfused with the fresh infusate from the infusate channel 501 as the blood travels down the blood channel 503. The reinfusion maintains blood volume and maintains the blood hematocrit at a constant level. In other implementations, the reinfusion rates are controlled to vary the hematocrit level according to a doctor's prescription. The amount of convective transport attained is proportional to the amount of fluid introduced to the infusate channel 501 and the amount of fluid removed from the filtrate channel 502 through the outlet 508. In some implementations, pressures within the infusate channel 501, blood channel 503, filtrate channel 502, or any combination thereof are altered to control the net and total convection that occurs. In some implementations, the membrane properties can be adjusted to limit which molecules cross the membrane based on a molecular weight cut off or other properties of the membranes 504. For example, the membrane could be etched (to increase diffusion and convection through the membrane) or sealed (to decrease diffusion and convection through the membrane) to change the membrane's transport properties.

Each of the infusate channel 501 and the filtrate channel 502 include a valve 510 in-line with the pump 509. The valve 510 is one example of an active pressure control feature, which are also referred to herein as controllable flow control devices. Pressure control features can be active (e.g., the controllable valve 510) or passive (e.g., a fixed variation in channel diameter or a static porous membrane). The pressure control features can be placed toward the inlet and/or outlet (or anywhere along the fluidic circuit) of any of the infusate channel 501, the blood channel 503, and the filtrate channel 502. Referring back to the valves 510, each valve 510 is configured to adjust the pressure of the fluid between the outlet of the pump 509 and the inlet of the respective infusate channel 501 or filtrate channel 502. The valves 510 can also be configured to control the flow rate of the fluid entering the infusate channel 501 and the filtrate channel 502. The pressure entering the infusate channel 501 and the filtrate channel 502 can be set to control the pressure drop along each of the channels and provide the desired pressure profile along the infusate channel 501 and the filtrate channel 502. In some implementations, one of or neither of the infusate channel 501 and the filtrate channel 502 include a valve 510. In some implementations, the valve 510 is a variable, proportional flow valve. Referring to FIG. 3, the valve 510 can be controlled by the control system 300. For example, the control system 300 can set the valve 510 to different operational states that constrict or dilate a flow path through the valve 510.

Each of the substrates in which the infusate channel 501, the filtrate channel 502, and the blood channel 503 are defined in a thermoplastic such as, but not limited to, acrylic, polystyrene, polycarbonate. Each of the filtrate and infusate channels have a length of between about 5 cm and about 30 cm, about 10 cm and about 30 cm, about 15 cm and about 30 cm, or between about 20 cm and about 30 cm. The width of the filtrate and infusate channels are between about 300 µm and about 1000 µm or between about 750 µm and 1000 µm. The height of the channels is between about 10 µm and 500 µm or between about 10 µm and about 80 µm. In some implementations, each layer 102 includes a single infusate channel that spans a plurality of the blood flow channels. A device with a single, wide infusate channel can be used when the infusate in introduced to the blood through controlled infusion areas, for example, the microfluidic convective clearance device described below in relation to FIG. 8A.

In some implementations, one or more components of the device 500 are disposable and configured to withstand sterilization. For example, because the infusate flowing through the infusate channel 501 comes into contact with the blood in the blood channel 503, the substrates of the device 500 defining the infusate channel 501 and blood channel 503 may be sterilized prior to use and be disposed of after use.

Each of the infusate channel 501, the blood channel 503, and the filtrate channel 502 have a pressure profile. The pressure profile defines how the pressure changes along the length of each of the channels, which in turn defines the pressure differentials between the channels. This pressure differential can also be called the trans-membrane pressure. In some implementations, if the trans-membrane pressure (e.g., the relative pressure difference across a membrane) is too high for a given membrane, the membrane between the blood and the filtrate channels can clog with the particulate from the blood. The clogging of the membrane can result in a degradation of the performance of the device as fluid and particles cannot pass from the blood channel 503 to the filtrate channel 502. In some implementations, if the trans-membrane pressure differential is too low at any location along the length of the channel, the device underutilizes its ability to clear particles from the blood.

Maintaining a controlled transmembrane pressure (or trans-interchannel barrier pressure) along the length of the channels enables substantially the entire length of the channels to contribute to the convective clearance. Controlling the transmembrane pressure also protects areas of membrane from high transmembrane pressures that can damage the membrane. Controlling variation in trans-membrane pressure along the length of the channel within 50% provides for efficient use of the membrane with the full length of the membrane contributing to overall convective clearance while not sacrificing durability. This enables the use of less membrane within the device while promoting greater durability. In a traditional device, the transmembrane pressure varies widely along the length of the fiber or channel due to the countercurrent flow of dialysate and the relatively low pressure drop that results due to the open geometry of the dialysis chamber. This can result in variation in transmembrane pressure along the length of the fiber or channel of over 100%. For these devices, the transmembrane pressure is high at the channel inlets and low at the channel outlets. If the pressure profiles are controlled to prevent high transmembrane pressure from damaging the membrane at the proximal portion of the membrane, the distal portion of the membrane is exposed to low pressures and does not provide significant convective clearance. If the transmembrane pressure is allowed to exceed safe levels for the membrane to enable the distal portion of the membrane to contribute to convective clearance, the proximal portion of the membrane will foul and lead to premature failure of the filter.

As described above, lower variation in transmembrane pressure along the length of the channel can provide for efficient use of the membrane along the full length of the membrane. For example, the pressure difference between any two of the channels in the convective clearance device is controlled such that the pressure difference does not vary by more than 50% of the pressure difference between the two channels, and in other implementations the pressure difference is controlled at predetermined locations, such as at the inlet (or other upstream portion) of the channels. In some implementations, the pressure difference varies between about 0% and about 40%, about 0% and about 30%, about 0% and about 20%, about 0% and about 15%, about 0% and about 10%, or about 0% and about 5%.

In some implementations, the pressure profile at the inlet or outlet of the channels is controlled to prevent clogging of the membrane. For example, if the transmembrane pressure at a location is too high, the membrane can become clogged. However, a transmembrane pressure that is too low can result in lower convective flow performance. In some implementations, the pressure difference between any two of the channels in the convective clearance device is controlled such that the pressure difference along the length of the channels does not vary by more than 50% of the average pressure difference between the two channels. In some implementations, the pressure difference varies between about 0% and about 40%, about 0% and about 30%, about 0% and about 20%, about 0% and about 15%, about 0% and about 10%, or about 0% and about 5% of the average pressure difference between the two channels.

In some implementations, complementary pressure control features maintain a substantially constant pressure along the length of each channel. For example, the pressure control features may compensate for the loss or addition of fluid volume to a channel by decreasing or increasing the cross-sectional area of a channel. In some implementations, the pressure control features prevent or reduce a pressure drop that otherwise would occur along the length of the infusate channels by reducing the effective resistance through the channel. Similarly, increases in pressure along the filtrate channel can be reduced or prevented by reducing the effective resistance through the channel. In some implementations, the complementary pressure control features maintain parallel pressure profiles by maintaining a substantially constant pressure difference between adjacent channels. In these implementations, the pressure changes in each of the channels along their respective lengths; however, the transmembrane pressure differential remains substantially constant because each of the channels experience the same pressure drop along their respective lengths. In some implementations, the transmembrane pressure is deliberately deviated from substantially constant to adjust the amount of filtration or infusion that occurs upstream versus downstream with respect to the flow in the channels. The pressure control features can be added to the infusate channel, the filtrate channel, the blood channel, the membranes, or a combination thereof.

Controlling the pressures along the length of the channels can improve the performance of the device for convective flow. The devices described herein include pressure control features configured to control the transmembrane pressure between adjacent channels. The channels of the devices can include complementary pressure control features such that the pressure profiles for each of the channels remain parallel, or substantially parallel, along the length of the channels. For example, during the operation of the devices described herein the infusate channel can lose pressure along its length as fluid flows into the blood channel from the infusate channel. At the same time, the filtrate channel can gain pressure along its length as fluid volume flows from the blood channel and into the filtrate channel. The infusate channel can include a first set of pressure control features to compensate for the decrease in fluid and the filtrate channel can include a second set of pressure control features that are complementary to the first to compensate for the increase in fluid in the filtrate channel. Because the transmembrane pressure differential is a relative value, the transmembrane pressure can be controlled in a number of ways.

In addition to adding pressure control features to one or more of the channels and membranes in the convective clearance device, in some implementations the pressure control feature includes flow control logic that controls the rate of flow through one or more of the channel by controlling the throughput of the pumps 509. According to fluid mechanics, if flow increases through a known restriction (e.g., a channel), then the pressure differential required to cause that flow increases. In this way, the flow from the pump 509 can be increased to increase the pressure drop from inlet to outlet. In the same way, the flow from the pump 509 can be decreased to decrease the pressure drop from inlet to outlet. The pressure drop defines the bounds of the pressure profile within a channel. The rate at which the pumps 509 flow fluid through the channels can be automatically or manually adjusted to maintain a desired pressure profile through the channels of the convective clearance device. For example, the blood can be flowed through the blood flow channel at a rate safe for blood (e.g., a rate that causes minimal trauma and shear to the red blood cells). The rate of the infusate through the infusate channel may be decreased or increased until the pressure profile of the infusate is similar in slope to the pressure profile of the blood. The rate of the filtrate through the filtrate channel may be increased or decreased until the pressure profile of the filtrate is similar in slope to the pressure profile of the blood. Pressure sensors can be added to the proximal and distal portions of channels as required to provide feedback for adjusting the pressure profiles.

Figure 5A:
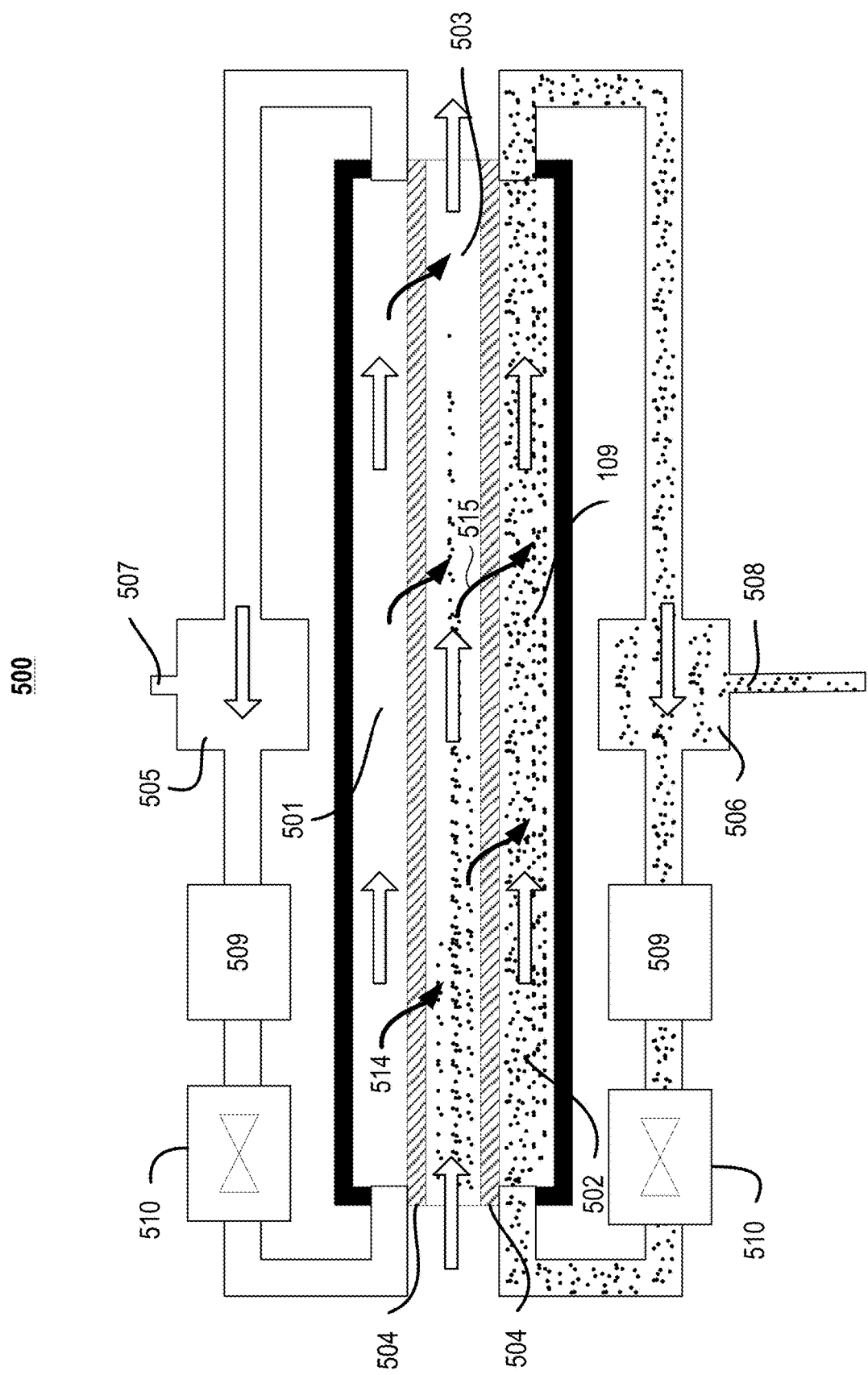
FIGS. 5A and 5B illustrate cross-sectional views of a microfluidic convective clearance device for use in hemofiltration.
Figure 5B:
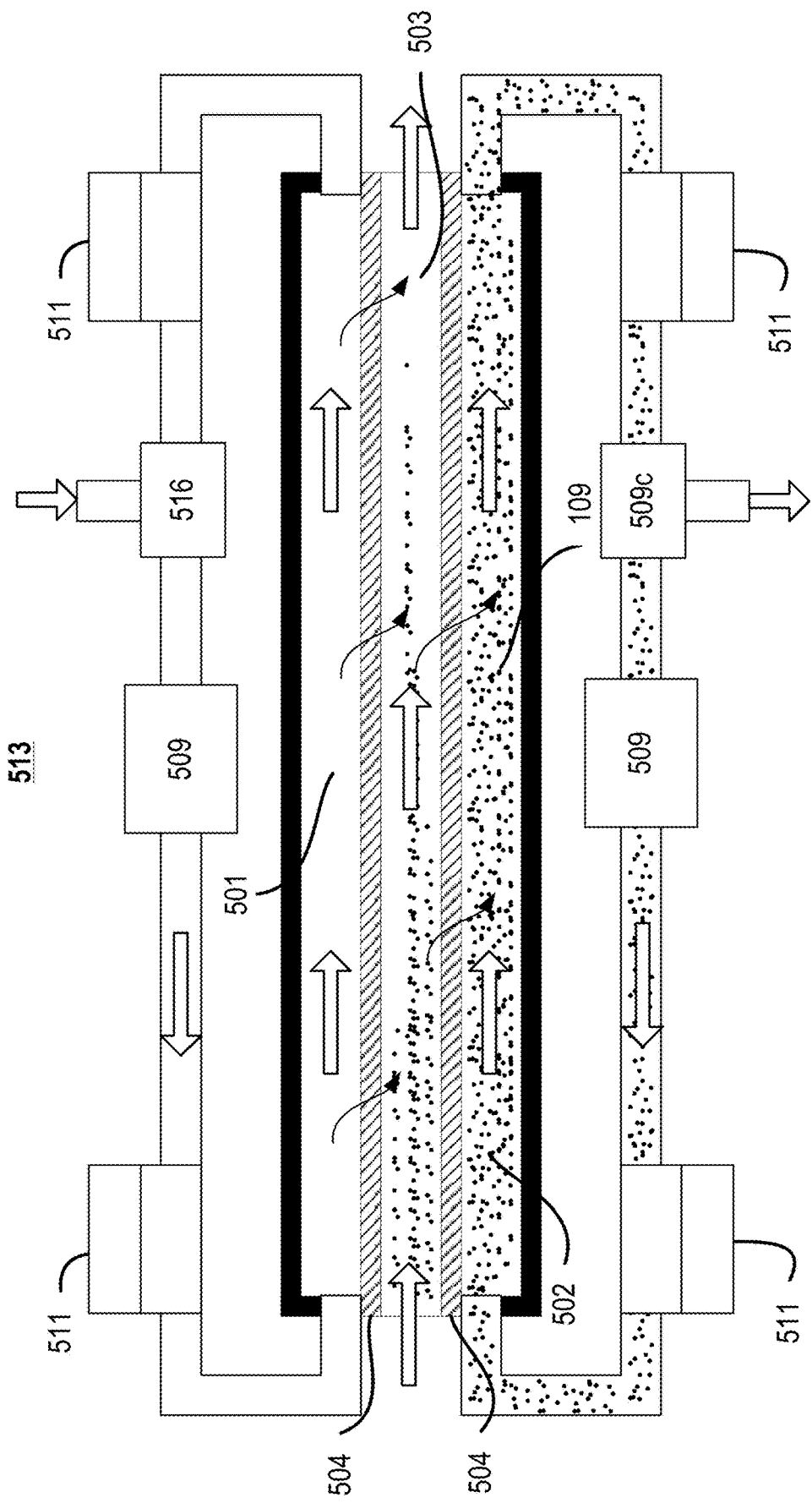

FIG. 5B illustrates a cross-sectional view of another microfluidic convective clearance device 513 for use in hemofiltration. The device 513 is similar to the device 500 described above in relation to FIG. 5A. The device 513 includes an infusate channel 501 and a filtrate channel 502 on either side of a blood channel 503. The blood channel 503 is separated from the infusate channel 501 and from the filtrate channel 502 by a membrane. A recirculating pump 509 is placed in-line with the infusate channel 501 and filtrate channel 502. The device 513 also includes a four diaphragm chambers 511. An influx pump 516 is in-line with the infusate channel 501 and pumps additional infusate into the infusate channel 501. The device 513 also includes an outflow pump 517 in-line with the filtrate channel 502. The outflow pump 517 is configured to draw filtrate out of the filtrate channel 502. The diaphragm chambers 511, influx pump 516, outflow pump 517, and recirculating pump 509 are each examples of active pressure control features.

The diaphragm chambers 511 are placed towards the inlets and outlets of the infusate channel 501 and the filtrate channel 502. The diaphragm chambers 511 are configured to set a predetermined pressure at each of the inlets and outlets to which they are coupled. Each of the diaphragm chambers 511 are coupled with a regulator and a pressure source. Increasing the pressure fed into the diaphragm chamber 511, via the regulator and the pressure source, increases the pressure in the fluid directly as it acts across the diaphragm. Decreasing the pressure fed into the diaphragm chamber 511, via the regulator and the pressure source, decreases the pressure in the fluid directly as it acts across the diaphragm. The recirculating pump 509 acts to transfer fluid from the lower pressure distal diaphragm chamber to the higher pressure proximal diaphragm chamber. The recirculating pump 509 can be controlled as a variable flow rate pump or activated intermittently when fluid volume in the proximal diaphragm chamber falls below a predetermined level. The amount of flow through the channel is determined by the geometry of the channels and the pressure conditions applied by the diaphragm chambers 511.

The influx pump 516 is configured to flow fresh infusate into the infusate channel 501. The outflow pump 517 is configured to flow an equivalent amount of filtrate out of the filtrate channel 502. By replenishing the infusate channel 501 and drawing the same volume of fluid from the filtrate channel 502, the influx pump 516 and the outflow pump 517 can maintain and control the hematocrit level within the blood channel of the device 513.

Figure 5C:
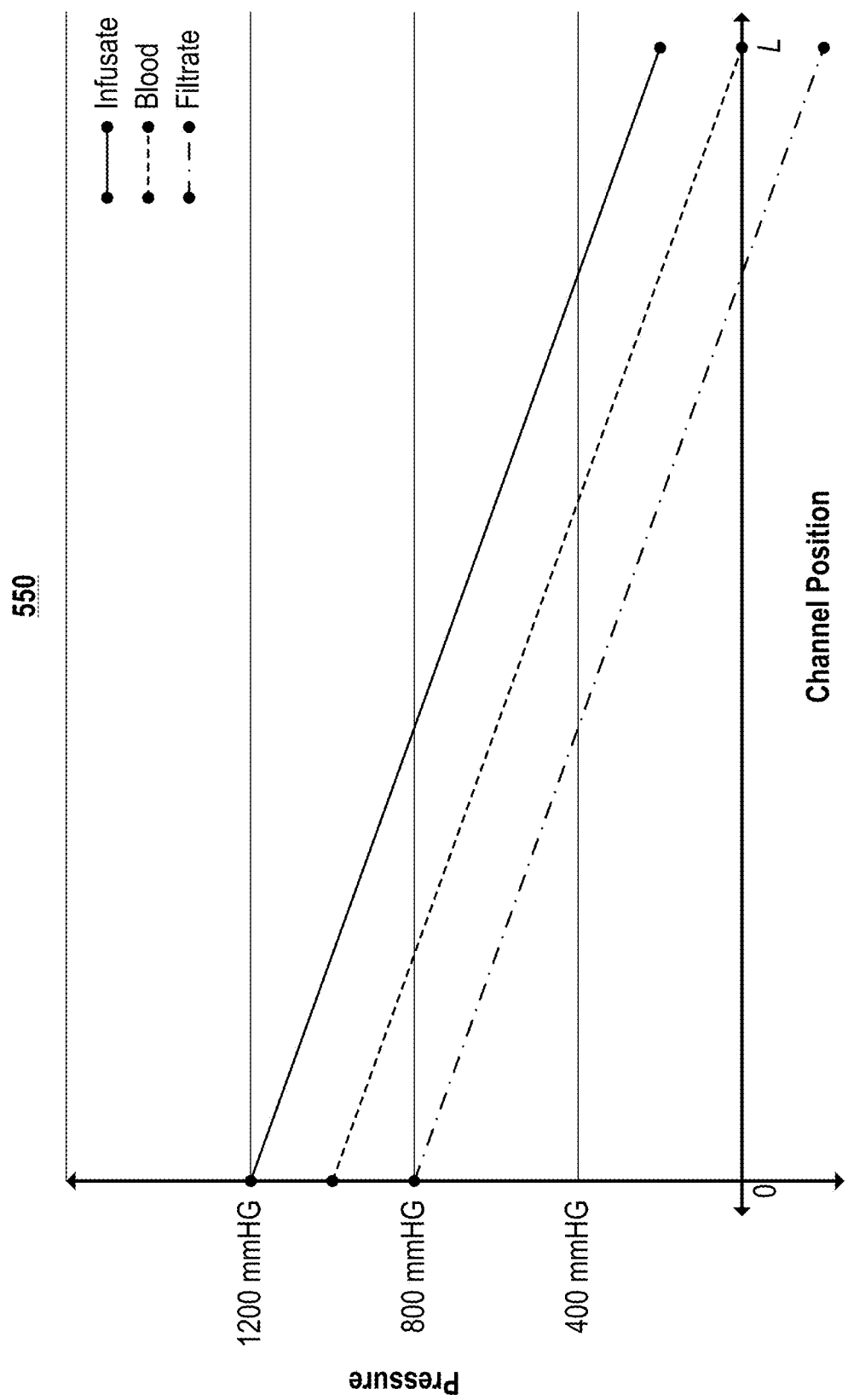
FIGS. 5C-5G illustrate graphs of example pressure profiles of each of the channels of microfluidic convective clearance device, such as that illustrated in FIGS. 5A and 5B.

FIG. 5C illustrates a graph 550 of an example pressure profile of each of the channels of device 500. The channel pressure is plotted along the y-axis and the channel position is plotted along the x-axis. FIG. 5C illustrates, assuming the length of the device 500 is L, that at the inlet to the infusate channel pressure is about 1200 mmHg, at the inlet to the blood channel the pressure is about 1000 mmHg, and at the inlet to the filtrate channel the pressure is about 800 mmHg. At each channel's outlet (channel position=L) the infusate channel pressure is about 200 mmHg, the blood channel pressure is about 0 mmHg, and the filtrate channel pressure is about −200 mmHg. In some implementations, the pressure difference between each of the channels is about 200 mmHg along the entirety of the channels. In other implementations, the pressure difference is between about 50 mmHg and about 400 mmHg, about 100 mmHg and about 350 mmHg, about 150 mmHg and about 300 mmHg, or about 200 mmHg and about 250 mmHg. In some implementations, the initial pressure of the blood channel is between about 400 mmHg and about 1200 mmHg, the initial pressure of the infusate channel is between about 600 mmHg and about 1400 mmHg, and the initial pressure of the filtrate channel is between about 200 mmHg and about 1000 mmHg. In some implementations, the final pressure of the blood channel is between about −200 mmHg and about 200 mmHg, the final pressure of the infusate channel is between about 0 mmHg and about 400 mmHg, and the final pressure of the filtrate channel is between about −400 mmHg and about 0 mmHg. As illustrated each of the pressure profiles each have the same slope and are parallel to one another. In some implementations, as illustrated in FIG. 5C, the slope of the pressure profiles is constant and the pressure profiles are linear.

The slope of the pressure profiles, the distance between the pressure profiles, and the shape of the pressure profiles can be controlled using the pressure control features described herein. For example, for the convective clearance device generating the graph 550, the blood may first be flowed through the convective clearance device. As described above, the rate of flow of the infusate and filtrate through the channels is adjusted to generate the desired pressure differential between the infusate and blood channels and the filtrate and blood channels. For example, the infusate may be flowed through the convective clearance device channels at a relatively lower or higher rate compared to the blood and the filtrate may be flowed through the convective clearance device at a relative higher or lower rate compared to the blood. These flow rates can depend on the cross section area of the channels. In relation to FIG. 5C, the rate of flow of the infusate and filtrate through the channels influences the slope of the respective pressure profiles on the graph 550. The flows through the filtrate and infusate channels are controlled by pumps 509 or other pressure control feature. The flow of the infusate into the inlet 507 and the flow of the filtrate out of the outlet 508 influence the vertical position of the respective pressure profiles on the graph 550. The slopes and/or shapes of the infusate and filtrate channels can also be tuned using one or more of the pressure control features described herein. The vertical positions of the pressure profiles can be controlled by additional pumps. For example, additional pumps at the outlet 508 or inlet 507 can be used to draw a net pressure differential between infusate and blood or filtrate and blood channels. As illustrated on the graph 550, a 200 mmHg net vacuum is applied to the filtrate channel. The vacuum shifts vertical position of the filtrate pressure profile down, enabling the filtrate pressure profile to match the blood pressure profile in slope, yet have an overall lower pressure resulting in flow from blood through membrane into the filtrate. The slope of the pressure profiles can further be adjusted by varying the resistance to flow through the channel or the resistance to flow through the interchannel flow barriers along the length of the channels. As described below, additional pressure control features can be added to the filtrate channels, infusate channels, the membranes, or any combination thereof to further alter the shape of the pressure profiles.

Figure 5D:
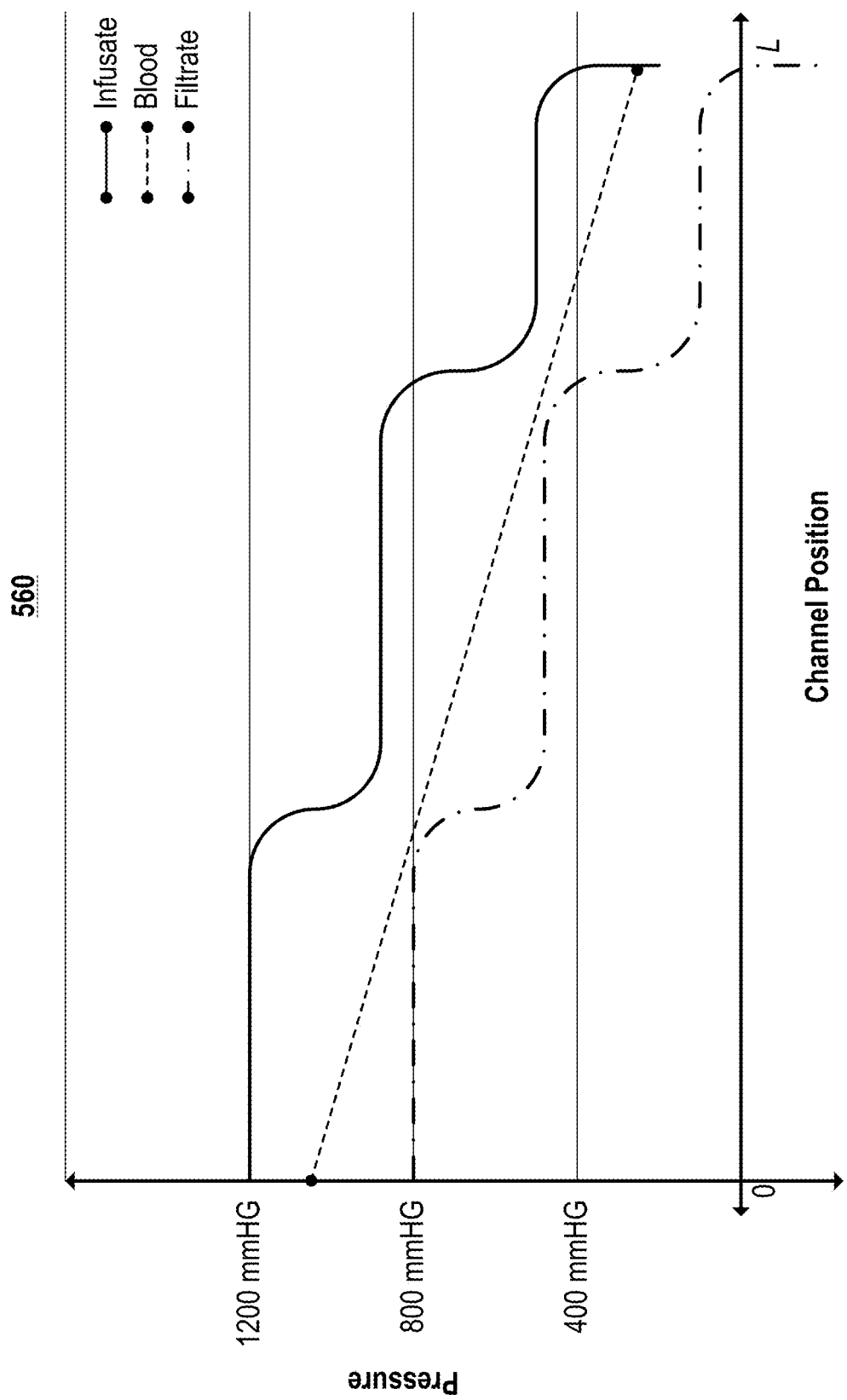

FIG. 5D illustrates a graph 560 of another example pressure profile of each of the channels in an example convective clearance device. As illustrated, the example pressure profiles of the filtrate channel and infusate channels are stair-stepped, and the blood channel pressure profile is substantially linear. The pressure in each of these channels may stay relatively constant and then step down at predetermined positions along the length of the channel. The step down in pressure may occur where the channel includes a pressure control feature. For example, as described further below, the complementary pressure control features may include a decreasing cross-sectional area in the infusate channel and an increasing cross-sectional area in the filtrate channel. The cross-sectional area of the infusate and filtrate channel of the example convective clearance device used to generate the graph 560 may change at two locations—resulting in a down-step in on the pressure profile at those locations of the changes in cross-sectional area. For example, the complementary pressure control feature in the infusate and filtrate channels may include individual infusate and filtrate zones. As described above in relation to the linear pressure profiles, the complementary pressure control features control the pressure difference between adjacent channels. In some implementations, the blood channel also includes a stair-stepped pressure profile.

In some implementations, the pressure profiles of the filtrate, blood, and infusate are substantially linear; however, the control system controls the pressure control features to maintain different transmembrane pressures at the proximal and distal ends of the convective clearance device. For example, the control system, via the pressure control features, can manipulate the slope of one of the filtrate, blood, and infusate pressure profiles to generate pressure profile biases toward the inlet or outlet of the device. In a "post-dilution bias," the slope of the pressure profiles of the infusate channel and the filtrate channel are less steep than the slope of the pressure profile of the blood channel. In contrast, in a "pre-dilution bias" the slopes of the pressure profile of the infusate channel and the filtrate channel are more steep than the slope of the pressure profile of the blood channel. The slope of the pressure profiles, the distance between the pressure profiles, and the shape of the pressure profiles can be controlled using the pressure control features described herein.

In some implementations, in a post-dilution bias configuration, the pressure control features maintain a substantially constant pressure difference between the pressures within the infusate channel and the filtrate channel, which makes the infusate pressure profile and the filtrate pressure profile substantially parallel. In the post-dilution bias configuration, the trans-interchannel flow barrier pressure difference between the infusate and blood channels is less toward the beginning of the device and greater toward the end of the device. The trans-interchannel flow barrier pressure difference between the filtrate and blood channels is greater toward the beginning of the device and less toward the end of the device. In this configuration less infusate fluid infuses into the blood at the beginning of the device, resulting in a higher concentration of solutes passing into the filtrate chamber along the length of the device. In some implementations, the post-dilution bias configuration can provide an overall greater amount of convective clearance when compared to the pre-dilution bias configuration.

In a pre-dilution bias configuration, the transmembrane pressure difference between the infusate and blood channels is greater toward the inlet of the device and less toward the outlet of the device. In contrast, the transmembrane pressure difference between the filtrate and blood channels is less toward the inlet of the device and greater toward the outlet of the device. In this configuration, more infusate fluid infuses into the blood toward the inlet of the device, but a lower concentration of solutes passes into the filtrate chamber from the blood along the length of the device. The lower concentration of solutes passing into the filtrate chamber can result in an overall lower amount of convective clearance when compared to the post-dilution bias configuration, but the pre-dilution bias configuration can result in a lower average hematocrit within the device and an increased reliability.

Figure 5E:
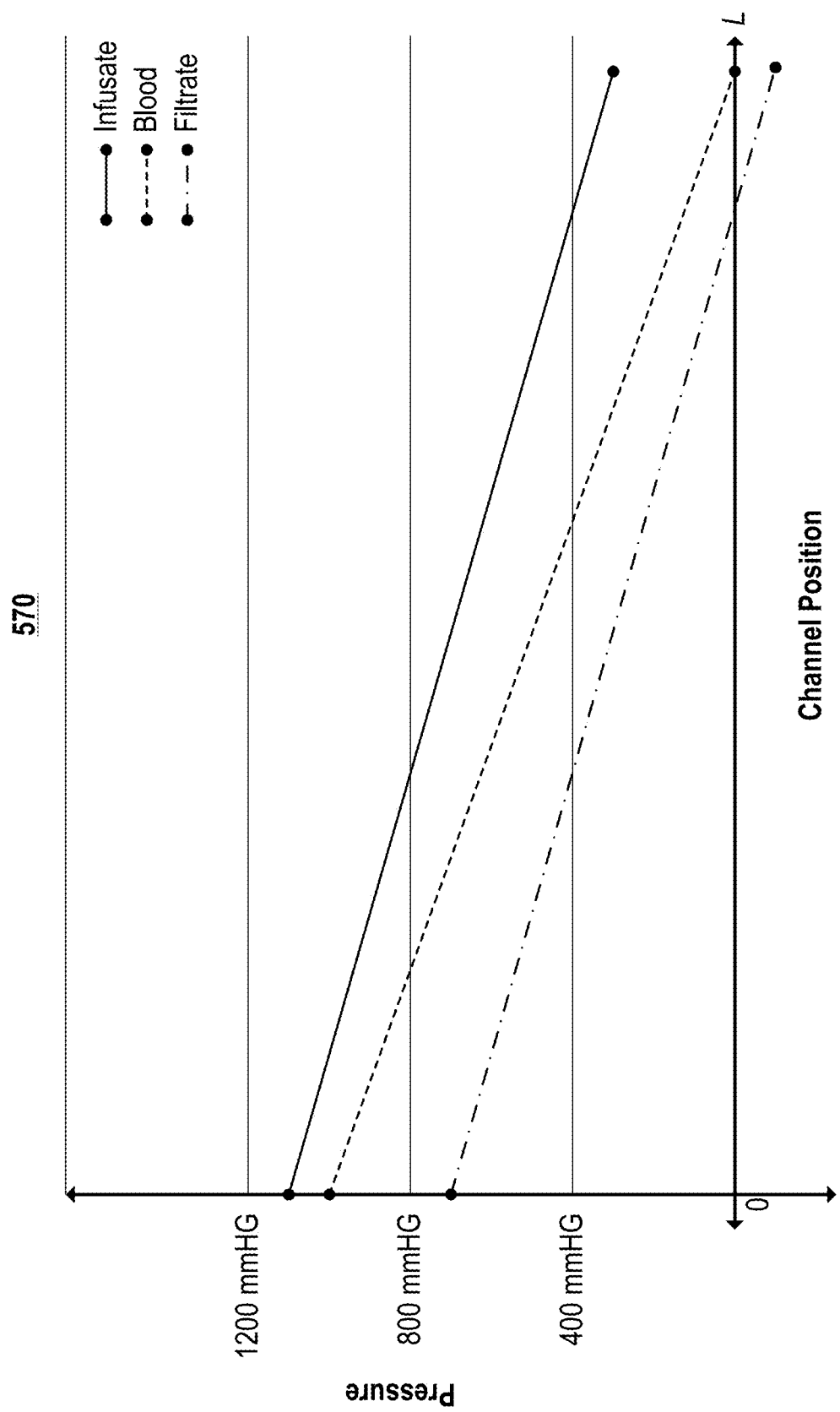

FIG. 5E illustrates a graph 570 of another example pressure profile of each of the channels in an example convective clearance device. As illustrated, the example pressure profiles the of infusate and filtrate channels are substantially parallel. The magnitude of the slope of the blood channel's pressure profile is more steep (e.g., greater) than the magnitude of the slope of the infusate and filtrate's pressure profile. As, illustrated the different slopes cause a post-dilution bias, as there is a greater pressure difference between the blood and filtrate pressure profiles towards the inlet of the convective clearance device when compared to the outlet of the convective clearance device.

Figure 5F:
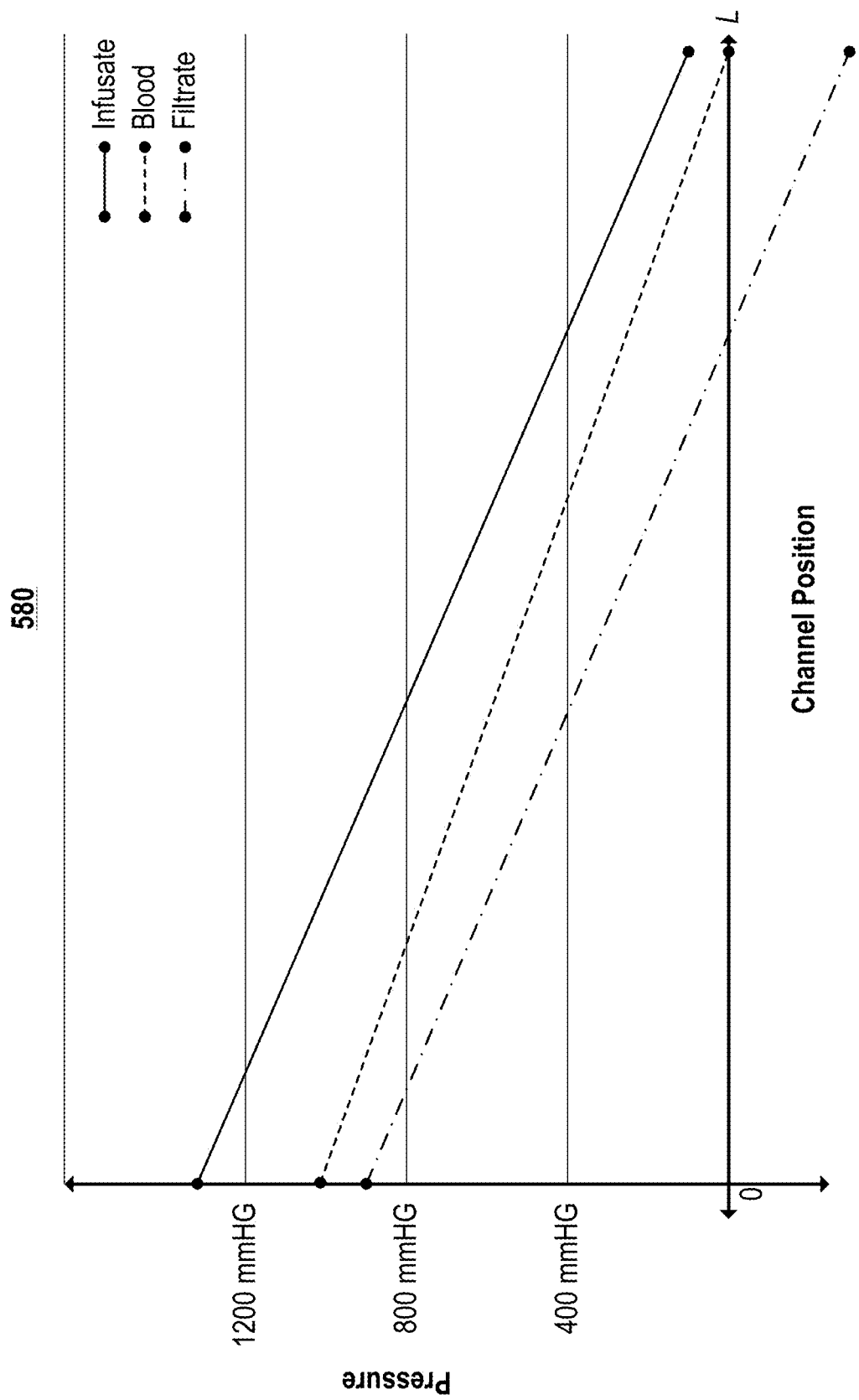

FIG. 5F illustrates a graph 580 of another example pressure profile of each of the channels in an example convective clearance device. As illustrated, the example pressure profiles of the infusate and filtrate channels are substantially parallel. The magnitude of the slope of the pressure profiles of the infusate channel and the filtrate channel are relatively more steep (e.g., greater) than the magnitude of the slope of the pressure profile of the blood channel. As, illustrated the different slopes cause a pre-dilution bias as there is a smaller pressure difference between the blood and filtrate pressure profiles towards the inlet of the convective clearance device when compared to the outlet of the convective clearance device.

Figure 5G:
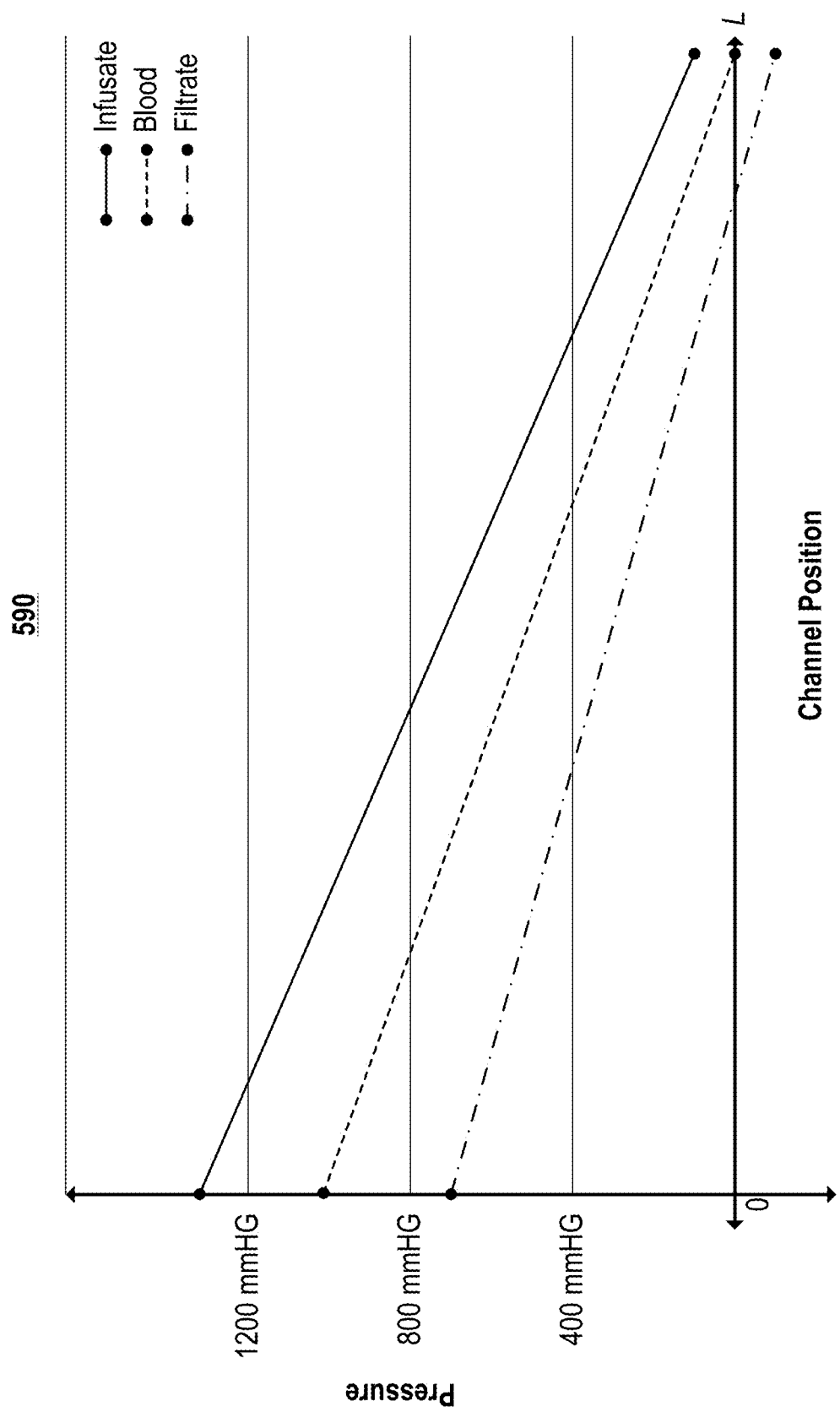

FIG. 5G illustrates a graph 590 of another example pressure profile of each of the channels in an example convective clearance device. The pressures within the filtrate and infusate channels are controlled independently of one another. This configuration can result in filtrate and infusate pressure profiles with different slopes. As illustrated, the example pressure profile of the infusate channel is steeper than the example pressure profile of the filtrate channel. Controlling the infusate and filtrate pressure profiles independently of one another can improve the performance and reliability of the device. As illustrated, the infusate channel is operated in a pre-dilution configuration to decrease hematocrit within the device, and the filtrate channel is operated in a post-dilution configuration to increase the solute concentration of the removed filtrate.

Figure 6A:
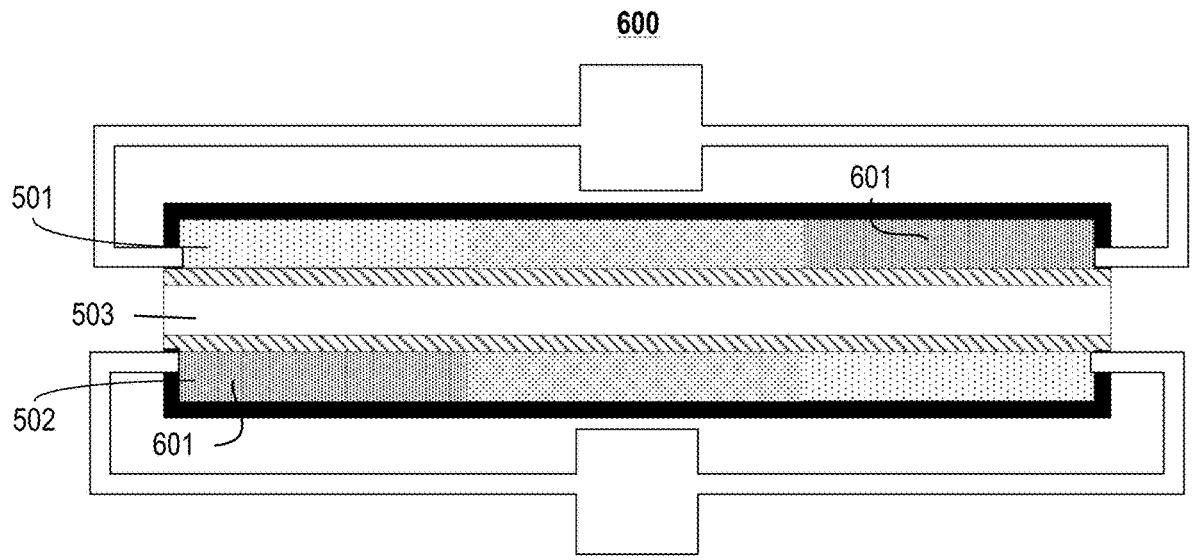
FIGS. 6A-6D illustrate cross-sectional views of example microfluidic convective clearance devices that include elements to compensate for pressure drop along the length of the device.
Figure 6B:
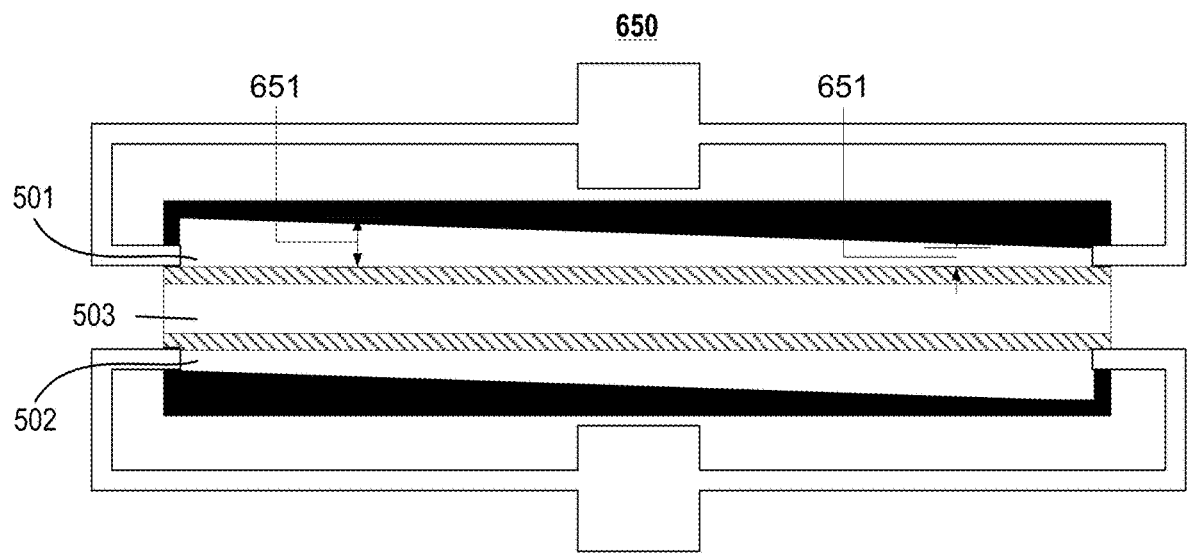

FIGS. 6A and 6B illustrate cross-sectional views of example microfluidic convective clearance devices that includes elements to compensate for fluid volume changes in the channels along the length of the device. FIG. 6A illustrates a device 600 that includes a flow restricting material 601 within the infusate channel and filtrate channel, and FIG. 6B illustrates a device 650 with a tapering channel design.

Referring to FIG. 6A, the device 600 includes an infusate channel 501, a blood channel 503, and a filtrate channel 502. The infusate channel 501 and filtrate channel 502 are filled with a material 601 that is restrictive to fluid flow and is an example pressure control feature. The material 601 can be a porous material, a mesh, a material consisting of sintered or packed particles, or an absorbent material. For example, the material 601 may include a plurality of packed particles, the volume of the particles occupies space within the infusate channel. The volume consumed by the packed particles causes the channel to behave similar to a narrower channel. Effectively narrowing the channel results in an increased pressure that counteracts the pressure drop that would be experienced as the infusate passes from the infusate channel to the blood channel. In other terms, the packed particles cause the porosity of the channel to decrease, which increases the resistance (R) of the channel.

Along the length of the channel, the flow (Q) through the channel changes because fluid flows into or out of the channel through the membrane. For example, flow through the infusate channel decreases along the length of the infusate channel as fluid flows across the membrane from the infusate channel to the blood channel. The pressure (P) in the infusate channel is about equal to QR. The porosity of the material 601 is controlled to give the proper R to affect the desired pressure profile curve. In other implementations, the channels include mechanical elements such as posts, ribs, struts, bumps, or other protrusions that result in resistance to flow. In some implementations, the material 601 is located at specific regions of the infusate and filtrate channels. In some implementations (as illustrated in FIG. 6A), the material 601 fills substantially the entire length of the infusate channel 501 and/or filtrate channel 502, and the fluid resistivity of the material 601 varies along the length of the channel to create a pressure gradient along the length of the channels. For example, the material 601 in the infusate channel 501 may include packed particles, the packing density of which increase along the length of the channel causing the channel to be more resistive along its length to flow. The increase in resistance along the length of the channel compensates for the loss of fluid flowing from the infusate channel 501 and into the blood channel 503, for example. The material 601 within the filtrate channel 502 is configured to decrease in resistance along the length of the channel to compensate for the increase in fluid volume received from the blood channel. In some implementations, when the material 601 runs the length a channel, the membrane can be glued or placed directly onto the material 601 with a low pressure epoxy. In some implementations, the device 600 can include any of the active pressure control features described herein.

FIG. 6B illustrates device 650 that includes channels with different cross-sectional areas. As illustrated, the height 651 (and/or width) of the infusate channel 501 and filtrate channel 502 change along the length of the channels. The changing height, width, or cross-sectional area of the channel is another example pressure control feature. The infusate channel becomes shallower toward the end of the channel, which results in an increase in fluid pressure within the infusate channel. In some implementations, the height and/or width of the channel may be changed to affect the pressure within the channel. In some implementations, the tapering of the channel height occurs along the entire length of the channel, as illustrated in FIG. 6B, and in other implementations, the tapering of the channel occurs only at predetermined locations. For example, the last ⅓ of the infusate channel may taper toward the infusate channel outlet. The filtrate channel 502 also includes the pressure control feature of a tapering height. The pressure control features of the infusate channel 501 and the filtrate channel 502 are complementary to one another in that as the cross-sectional area of the infusate channel 501 decreases, the cross-sectional area of the filtrate channel 502 increases to maintain parallel pressure profiles within the channels of the device 650. Smaller cross-sectional areas have higher resistance to flow compared to larger cross-sectional areas, and the resistance to flow based on cross-sectional area can be calculated according to Hagan-Poiseuille flow. Using the above described equation (P=QR) for the pressure along the length of each channel, the pressure (P) within each channel can be controlled by adjusting the cross-sectional area to achieve the desired R. In some implementations, the device 650 can include any of the active pressure control features described herein.

Figure 6C:
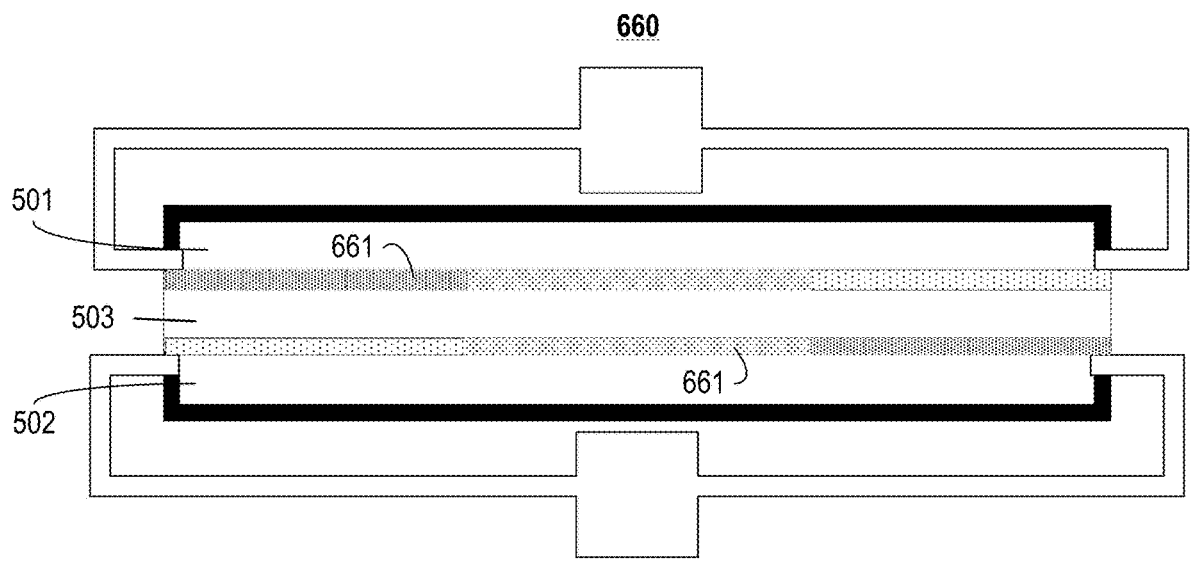

FIG. 6C illustrates device 660 that includes membranes 661 designed such that a property of the membrane changes along the length of the channels. The membranes 661 are configured to enable different levels of fluid transport at different positions along the length of the channels. Changing the property of the membrane is another example pressure control feature. The membrane 661 between the infusate channel 501 and the blood channel 503 is configured to decrease in porosity along its length, making it more difficult for fluid to pass through the membrane 661 towards the end of the infusate channel 501. The membrane 661 between the blood channel 503 and the filtrate channel 502 complements the membrane 661 between the infusate channel 501 and the blood channel 503. The membrane 661 between the blood channel 503 and the filtrate channel 502 increases in porosity along its length, making it easier for fluid to pass through the membrane 661 toads the end of the filtrate channel 502. Other properties of the membrane 661 that can be altered to affect transmembrane pressure can include, but are not limited to, the composition of the membrane, the application of a sealant to portions of the membrane, the size of the finger-void area of the membrane, or any other component in the membrane cross section which impacts flow across the membrane surface. For example, a portion of the membrane may be heated to seal the pores of the membrane and prevent transport across the membrane. In some implementations, the device 660 can include any of the active pressure control features described herein.

Figure 6D:
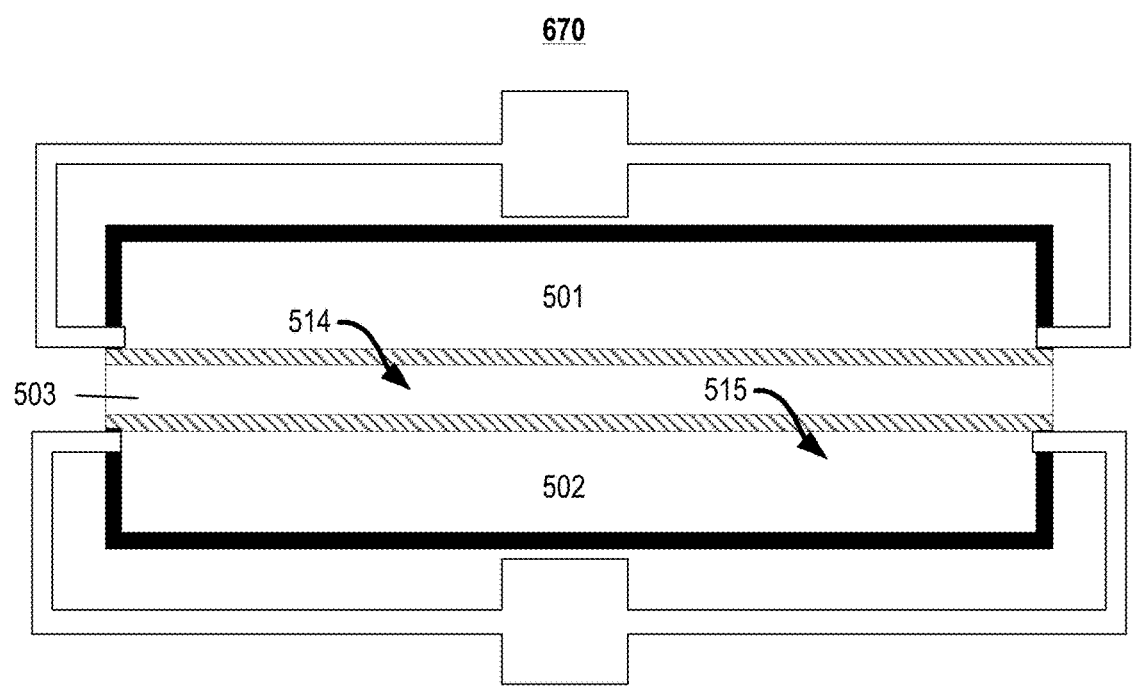

FIG. 6D illustrates a device 670 that includes channels configured to maintain substantially linear pressure profiles along their respective lengths. Each of the infusate channel 501, the filtrate channel 502, and the blood flow channel 503 have a constant geometry along their respective lengths. To maintain the substantially linear pressure profiles, the fluid flow through the infusate channel 501 and the filtrate channel 502 is substantially greater than the the flow 514 from the infusate channel 501 to the blood channel 503 and the flow 515 from the blood channel 503 to the filtrate channel 502. In this implementation, the pressure drop in the infusate channel 501 and the filtrate channel 502 remains substantially linear. In some implementations, the flow through the infusate channel 501 and the filtrate channel 502 is about 2 to about 8 or about 4 to about 6 times greater than the flow into or out of the infusate and filtrate channels respectively to channel 503. In some implementations, the device 670 can include any of the active pressure control features described herein.

In some implementations, the channels may include features to reduce the flexion of the membranes. The features can include discrete features such as posts, chevrons, pyramids, hills, textured fields, or ribs; or continuous support mediums such as porous media, screens, through-hole etched thin films, secondary membranes, and sintered materials. The device may include one or more of the support features or a combination of discrete features and support mediums. In some implementations, the membrane support features prevent the membranes from deflecting under an applied transmembrane pressure while also allowing filtrate to flow freely through the membrane. Maintaining the position of the membranes can enable the blood channel to maintain its shape during the operation of the device—preserving shear rates in the blood channel.

Figure 7:
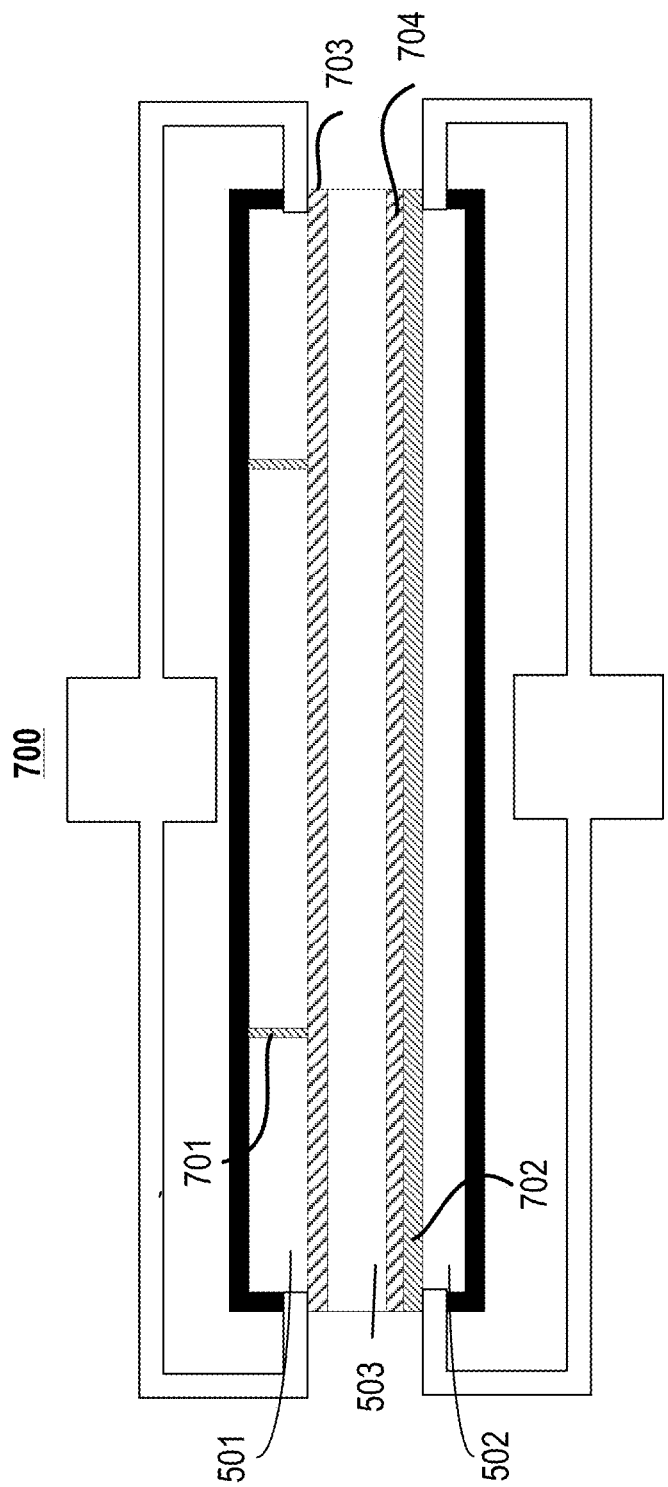
FIG. 7 illustrates a cross-sectional view of a microfluidic convective clearance device with membrane support features.

FIG. 7 illustrates a cross-sectional view of a microfluidic convective clearance device 700 with membrane support features. The device 700 includes posts 701 that maintain the height of the blood channel 503 by securing the membrane 703 to the ceiling of the infusate channel 501. The device 700 also includes a screen 702 that supports the membrane 704, and prevents the membrane 704 form flexing into the filtrate channel 502 as fluid flows from the blood channel 503 to filtrate channel 502 through the membrane 704. For example, the screen 702 is less flexible or elastic than the membrane 704. In some implementations, the screen 702 does not affect convection through the membrane 704. In other implementations, the screen 702 is configured to affect convection through the membrane 704. For example, the screen 702 may be a support structure with holes milled through the structure. The density of the holes can be altered along the length of the screen 702 to control the amount of convection that occurs through the membrane 704 coupled to the screen 702. In some implementations, the device 700 can include any of the active pressure control features described herein.

Figure 8A:
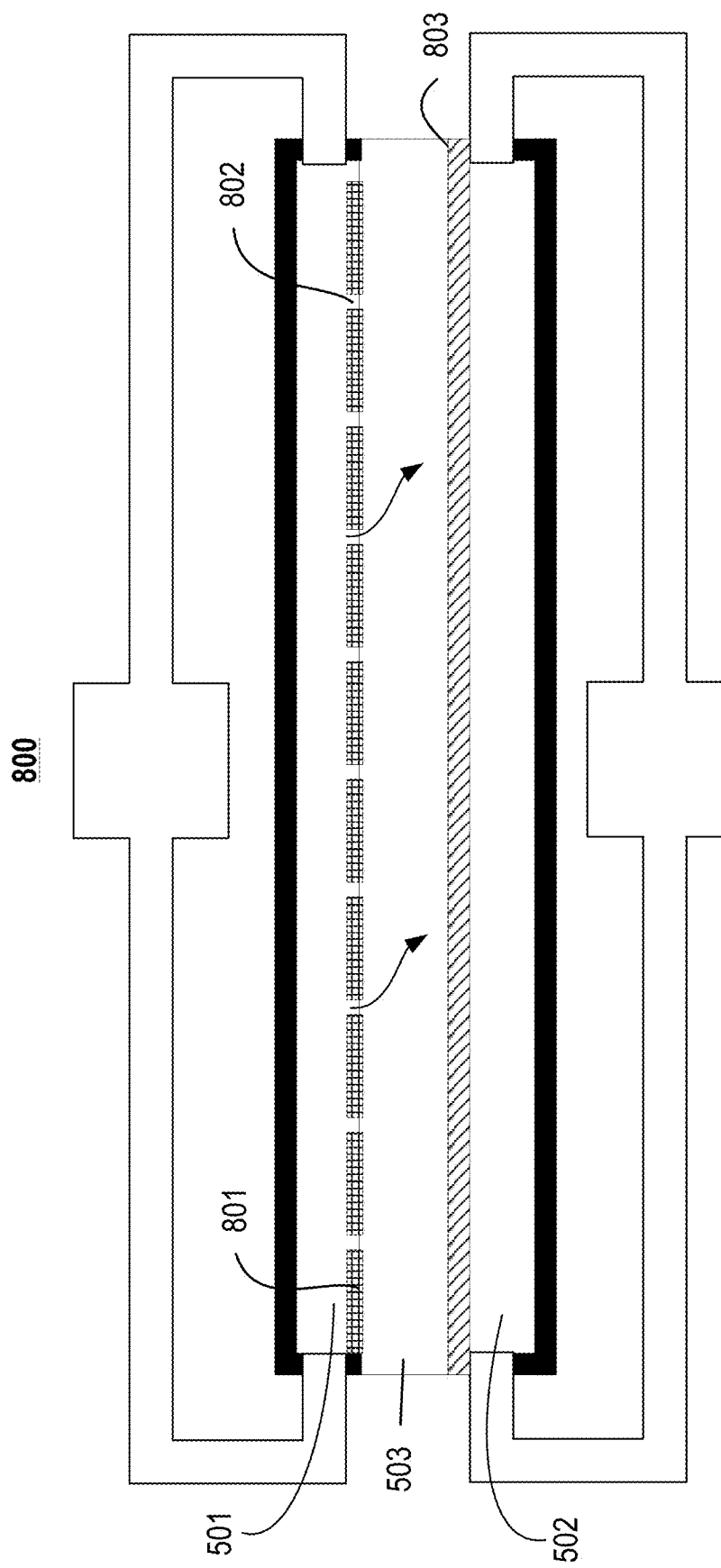
FIG. 8A illustrates a cross-sectional view along a length of a microfluidic convective clearance device with controlled infusion areas.

FIG. 8A illustrates a cross-sectional view along a length of a microfluidic convective clearance device 800 with controlled infusion areas. The device 800 includes a infusate channel 501 separated from a blood channel 503 by a non-porous material 801. The non-porous material includes a plurality of openings 802, which may also be referred to as apertures. The openings 802 are another example pressure control feature. In some implementations, the device 800 can include any of the active pressure control features described herein. A membrane 803 separates the blood channel 503 form the filtrate channel 502.

The openings 802 are machined across a face of a non-porous material 801 and provide fluidic communication between the infusate channel 501 and the blood channel 503. In some implementations, the openings 802 are fabricated into the non-porous material 801 material by molding, machining, laser drilling, punching, or track etching. In some implementations, the non-porous material 801 is a component of the substrate that defines one of the infusate channel 501 and the blood channel 503. For example, the non-porous material 801 may be the portion of the substrate defining the floor of the infusate channel 501. In some implementations, the infusate channel 501 and the blood channel 503 are defined on opposite sides of the same substrate, and the openings 802 are holes machined between the infusate channel 501 and the blood channel 503.

The non-porous material 801 includes a plurality of openings 802. The openings 802 can be placed at discrete locations or distributed over portions of the blood channel. In some implementations, the openings 802 have a pitch between about 1 cm and about 10 cm, about 4 cm and about 8 cm, or about 4 cm and about 6 cm. The openings 802 are placed in the non-porous material 801 above the blood channel at locations such that the infusion of liquid at the openings 802 can shape the hematocrit profile in the blood channel. In some implementations, the hematocrit profile is controlled by controlling the size and distribution of the openings 802. The non-porous material 801 with the openings 802 provide both the characteristics of a membrane as well as an access point for infusion. The infusion flow distribution into the blood channel 503 can be customized by changing the size, distribution, and length of each opening 802 relative to another opening 802.

Figure 8C:
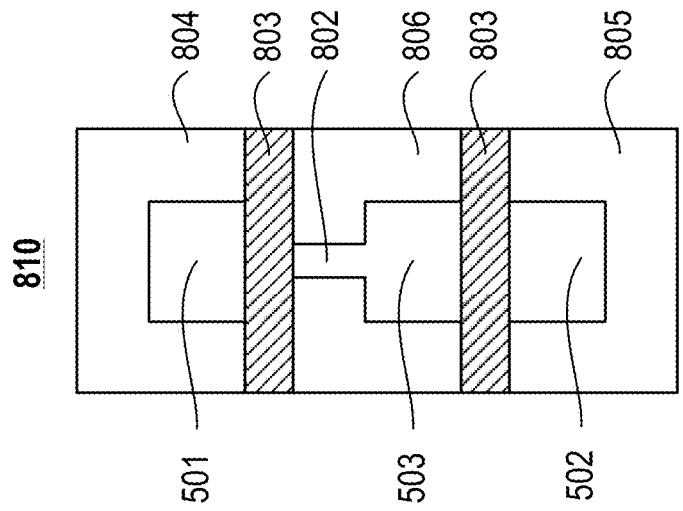
FIGS. 8B and 8C illustrate a cross-sectional view across a width of the microfluidic convective clearance device illustrated in FIG. 8A.
Figure 8B:
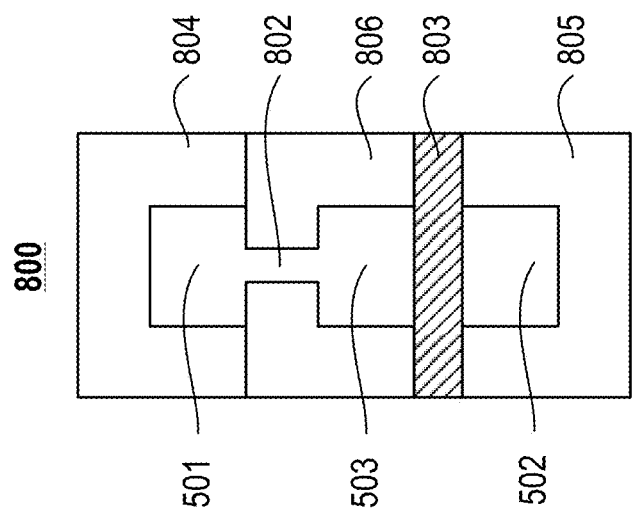

FIG. 8B illustrates a cross-sectional view across a width of the microfluidic convective clearance device 800 with controlled infusion areas illustrated in FIG. 8A. The device 800 includes an infusate channel 501 and a blood channel 503 separated by an opening 802. A filtrate channel 502 is separated from the blood channel 503 by a membrane 803.

The infusate channel 501 of the device 800 is defined in a first substrate layer 804, the blood channel 503 is defined in a second substrate layer 806, and the filtrate channel 502 is defined in a third substrate layer 805. The channels are defined in their respective substrates through photolithographic techniques, injection molding, direct micromachining, deep RIE etching, hot embossing, or any combinations thereof. The substrate layers 804, 805, and 806 include a thermoplastic such as, but not limited to, acrylic, polystyrene, polycarbonate, or any of the other materials described herein. The openings 802 are machined (e.g., laser drilled) into a wall of the infusate channel 501. The openings 802 have a diameter between about 1 μm and about 300 μm, between about 100 μm and about 250 μm, or between about 150 μm and about 200 μm. In some implementations, each of the layers of the device 800 are secured together with a bonding agent, such as a glue or epoxy, and in other implementations, the layers are clamped together.

FIG. 8C illustrates a cross-sectional view across a width of another example convective clearance device 810. The convective clearance device 810 is similar to the convective clearance device 800, and includes a first substrate 804, a second substrate 806, and a third substrate 805 defining an infusate channel 804, a blood channel 805, and a filtrate channel 502, respectively. The convective clearance device 810 includes two membranes 803. The first membrane 803 separates the infusate channel 501 from the blood channel 503, and the second membrane 803 separates the blood channel 503 from the filtrate channel 502. The first membrane 803 sits atop the second substrate 806 and the openings 802 defined therein. In some implementations, the spacing of the openings 802 is selected to control the diffusion through the membrane 803. For example, the openings 802 can be more closely spaced toward the end of the infusate channel 501 to enable greater transport through the membrane 803. The effective membrane area of the first membrane 803 can be increased with slots or pockets around the opening 802 in the non-porous material 801 For example, the cross-sectional area of the openings 802 can be increased to compensate for low pressure differences across the membrane 803 and enable more transport across the membrane 803. The cross-sectional area of the openings 802 can be decreased to compensate for high pressure differences across the membrane 803, which restricts the amount of convection across the membrane 803.

Figure 9:
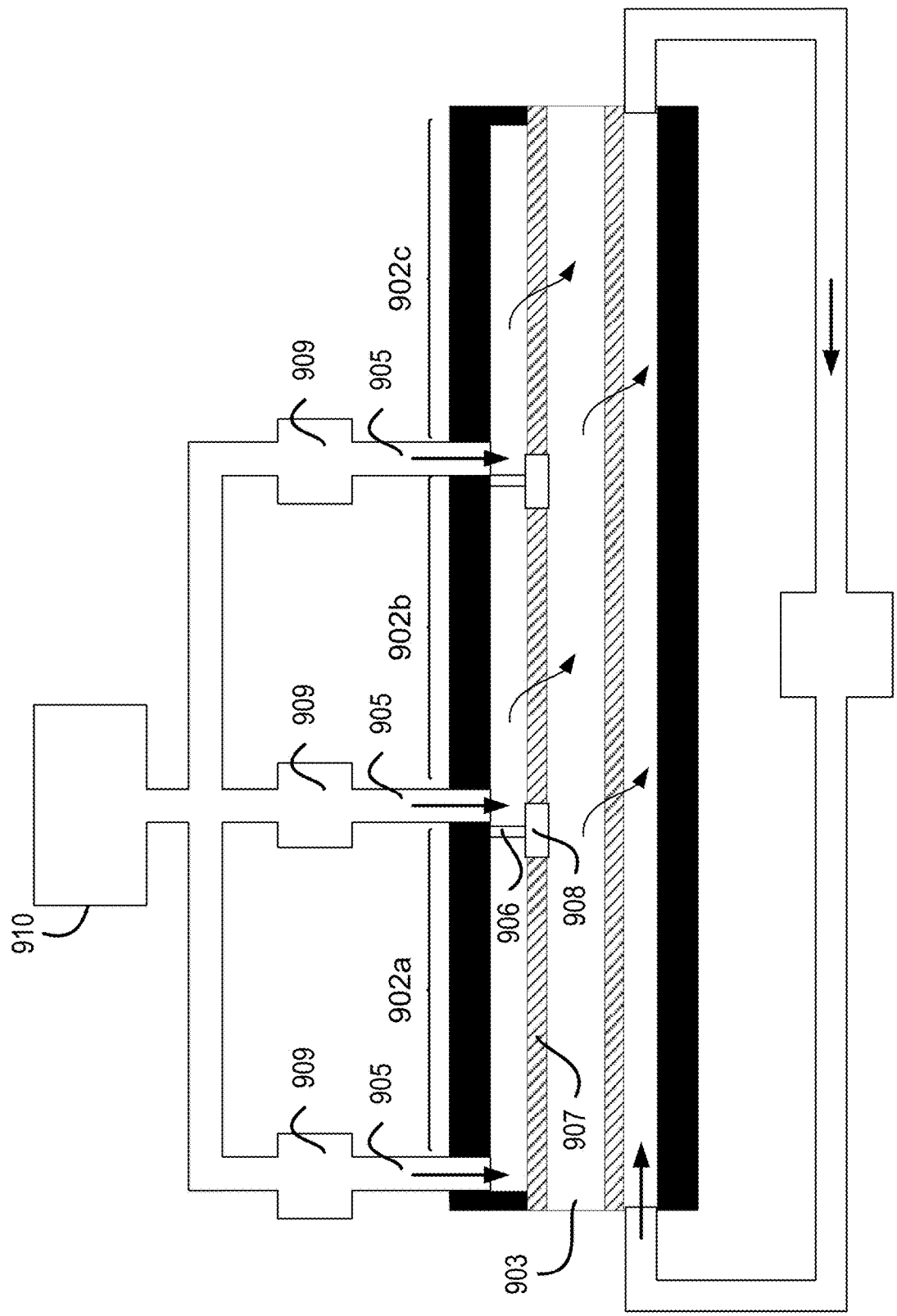
FIG. 9 illustrates a cross-sectional view of a microfluidic convective clearance device with infusion and filtration zones.

FIG. 9 illustrates a cross-sectional view of a microfluidic convective clearance device 900 with infusion zones. The different infusion zones are another example pressure control feature. The device includes three infusion zones 902a, 902b, and 902c (generally infusion zones 902) that are defined within an infusate channel. A distal end of each of the respective infusion zones 902 is defined by a intrachannel flow barrier 906. The intrachannel flow barriers 906 are coupled to a permeable membrane 907, and are specifically coupled to the permeable membrane 907 at sealed, non-porous portions 908 of the membrane 907. The intrachannel flow barriers 906 are substantially non-porous and prevent flow from one infusion zone 902 to the next through the infusate channel or through the finger voids of the membrane 907. The fluid entering each of the infusion zones 902 flows across the membrane 907 within the infusion zone 902 where the fluid was introduced to the device 900. The sealed, non-porous portions 908 of the membrane 907 can be formed by applying heat or an epoxy to the membrane 907 to seal or clog the pores of the membrane as well the finger void within the membrane. In some implementations, the portion of the membrane 907 within each of the different infusion zones 902 is configured differently. For example, the first portion of the membrane 907 within the first infusion zone 902a may have a higher porosity than compared to the portion of the membrane 907 in the last infusion zone 902c. In some implementations, the separate infusion zones 902 generate stair-stepped pressure profiles similar to those described in relation to FIG. 5D. In some implementations, the above-described zones are formed in the filtrate channel to create independent filtrate zones.

Each of the infusion zones 902 include an inlet 905. The inlet 905 supplies infusate to each of the respective infusate zones 902. Each inlet 905 is coupled to a pump 909, which are each connected to a central infusate reservoir 910. Each of pumps 909 are configured to operate independently of one another, such that the flow rate and pressure to each inlet 905 (and infusion zone 902) is individually controllable. For example, the pump 909 coupled to a last inlet 905 may flow infusate into to the infusion zone 902c at a lower pressure than compared to a pump 909 coupled to the first infusion zone 902a to account for a pressure decrease experienced toward the end of the blood channel.

Figure 10:
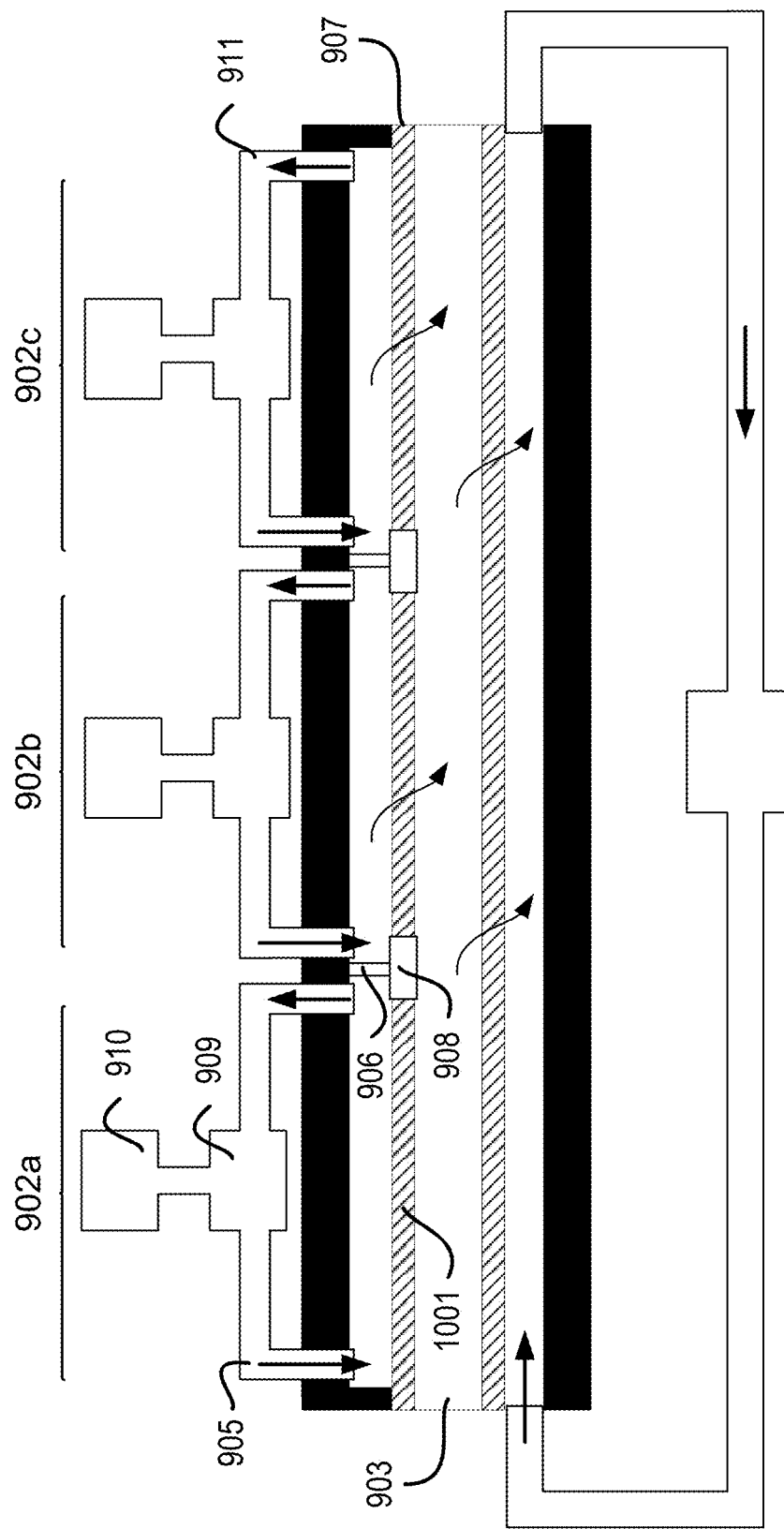
FIG. 10 illustrates a cross-sectional view of a microfluidic convective clearance device with individual chambers within the membranes.

FIG. 10 illustrates a cross-sectional view of a microfluidic convective clearance device 1000 with different infusion zones. As described above in relation to FIG. 9, the device 1000 includes an infusate channel that is divided into separate infusion zones 902a-902c. Each of the infusion zones 902 are separated by an intrachannel flow barrier 906, which is coupled to a non-porous portion of the membrane 907. Each infusion zone 902 includes an inlet 905 that is supplied with infusate from a reservoir 910 vi a pump 909. Each infusion zone 902 also includes an outlet 911 so that a portion of the fluid introduced into the infusion zone 902 passes through the membrane and a portion leaves through the outlet 911. The flow through the respective inlets 905 and outlets 911 can be controlled by respective pumps 909 to more finely control the pressures and infusion rate through the membrane 907 within each infusion zone 902.

In some implementations, the sections of membrane 907 within each of the infusion zones 902 are individual membrane portions 1001. In some implementations, each of the membrane portions 1001 are separate permeable membrane pieces coupled together to form a continuous membrane. Each of the membrane portions 1001 along the length of the channels can be configured differently. For example, each membrane portion 1001 can include a different porosity or be coated to change the permeability of the portion. In some implementations, the shape and density of the finger-voids within the membrane portions 1001 are controlled to affect the transport across the membrane portions 1001. The finger-voids are the voids on the interior of the membrane portions 1001. Larger finger-voids result in a less dense and less constrictive membrane portion 1001, and smaller finger-voids result in a denser and more restrictive membrane portion 1001.

In some other implementations, membrane portions 1001 are created by crimping, molding, or potting a permeable membrane to create individual chambers. In some implementations, molding is inserted around the membrane portions 1001 to prevent flow between membrane portions 1001. In some implementations, the crimp is created by forcing or potting the membrane onto a molded plate. Similarly, gluing, welding, or applying a solvent can be used to define membrane portions 1001 and prevent the lateral flow within the membranes. The glue bond or weld that forms each end of a portion 1001 is designed to prevent lateral flow between adjacent membrane portions 1001, while at the same time not disturbing the surface of the membrane portion 1001 facing the blood channel.

In some implementations, the transverse membrane pressure can also be controlled in any of the devices described herein by controlling the properties of the interchannel flow barriers along the length of the device. For example, the interchannel flow barrier separating the infusate channel and the blood channel may become more porous along the length of the channels to compensate for the decrease in pressure in the infusate channel as it loses volume to the blood flow channel. The change in porosity of the interchannel flow barrier can be controlled by controlling the thickness of the interchannel flow barrier along the length of the channel. For example, membranes can be stacked so that at the distal end, the membrane stack separating the infusate channel or filtrate channel from the blood channel includes only a single layer of membrane. Upstream, towards the proximal side of the device, additional layers of membrane are added to the membrane stack between the blood channel and the filtrate channel to add additional restriction to the vertical flow path. As the resistance of each membrane has an additive component in the stack, the pressures between the membranes is set so that no one membrane sees excessive transverse pressure. This has an effect of insuring that each individual membrane sees only the target pressure range in which it can function effectively. In another implementation, the pore size of the membranes can be varied along the length of the interchannel flow barrier to control the pressure drop. Epoxy or heat can be applied to the membrane at specific portions to control the restrictiveness of the interchannel flow barrier. Applying heat to a surface of the interchannel flow barrier can melt and seal the pores in the interchannel flow barrier. The amount of heat (or epoxy) can be controlled to regulate the percentage of pores that are sealed during the sealing process.

In some implementations, the properties of the membrane itself can be changed, so that portions of the membrane function effectively at higher pressure and some at lower pressure. Aligning properly to the channel yields an effective means to insure that membrane is behaving as desired.

Figure 11:
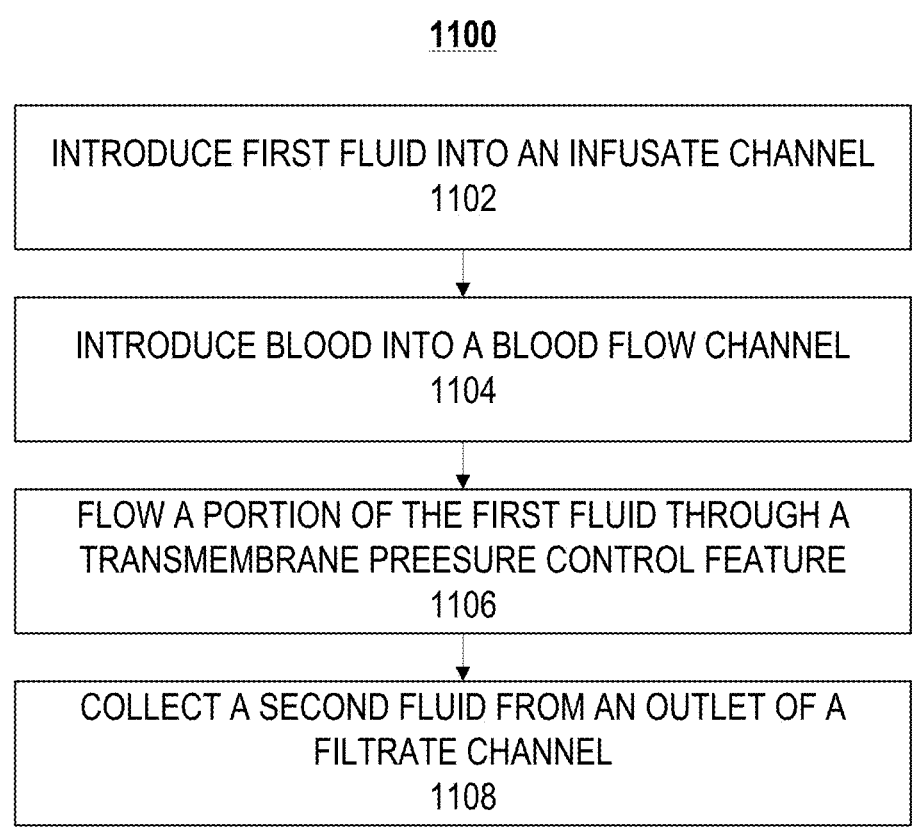
FIG. 11 illustrates a flow chart of an example method for cleansing a fluid using a microfluidic convective clearance device.

FIG. 11 illustrates a flow chart of an example method 1100 for cleansing a fluid. The method 1100 includes introducing a first fluid into an infusate channel (step 1102).

The method 1100 also includes introducing blood into a blood flow channel (step 1104). At least a portion of the first fluid is flowed through a pressure control feature (step 1106). The pressure control feature substantially parallelizes a pressure profile of the infusate channel and a pressure profile of the blood flow channel. That is, the pressure control feature renders the inter-channel pressure differential to be substantially constant along substantially the entire length of the channels. The method 1100 also includes collecting a second fluid from an outlet of a filtrate channel (step 1108).

As set forth above, the method 1100 includes introducing a first fluid into an infusate channel (step 1102). The infusate channel can be an infusate channel of any of the devices described herein, and the first fluid can be infusate. The method 1100 also includes introducing blood into a blood flow channel (step 1104). In some implementations, the blood and the infusate channels are parallel and complementary to one another. For example, the blood and the infusate channels overlap one another and are separated by a membrane or other interchannel flow barrier. In some implementations, the blood and the infusate are flowed through the device in the same direction. In some implementations, the infusate is introduced into the infusate channel at a relatively higher pressure than the blood is introduced to the blood flow channel.

The method 1100 also includes flowing a portion of the first fluid through a pressure control feature (step 1106). As described above, the pressure control feature can be a feature of the infusate channel and/or the interchannel flow barrier separating the infusate channel and blood channel. For example, the pressure control feature can be a tapering of the cross-sectional area of the infusate channel or a plurality of apertures defined in the interchannel flow barrier. In some implementations, the portion of the first fluid is driven through the interchannel flow barrier or the pressure control feature by the pressure gradient between the infusate channel and the blood channel. In some implementations, the blood channel and/or the filtrate channel also include a pressure control feature that substantially parallelizes the pressure profile of the blood channel with a pressure profile of the filtrate channel.

The method 1100 also includes collecting a second fluid from an outlet of a filtrate channel (step 1108). In some implementations, the second fluid is a filtrate that is flowed through a filtrate channel of the device. The filtrate channel can be complementary to the blood flow channel and be separated from the blood flow channel by a second interchannel flow barrier. The second fluid can be introduced to the device a pressure relatively lower than the pressure the blood is introduced to the device. The pressure differentials between the infusate channel, blood channel, and filtrate channel drives a portion of the infusate into the blood and then a portion of the blood into the filtrate channel—cleansing the blood. The portion of the blood driven into the filtrate channel can be plasma, urea, or other waste particles, and are generally referred to as particles. As the fluids flow through the device, the particles are driven into the filtrate channel. The filtrate (now including the particles) is collected as the filtrate exits the device.

Figure 12:
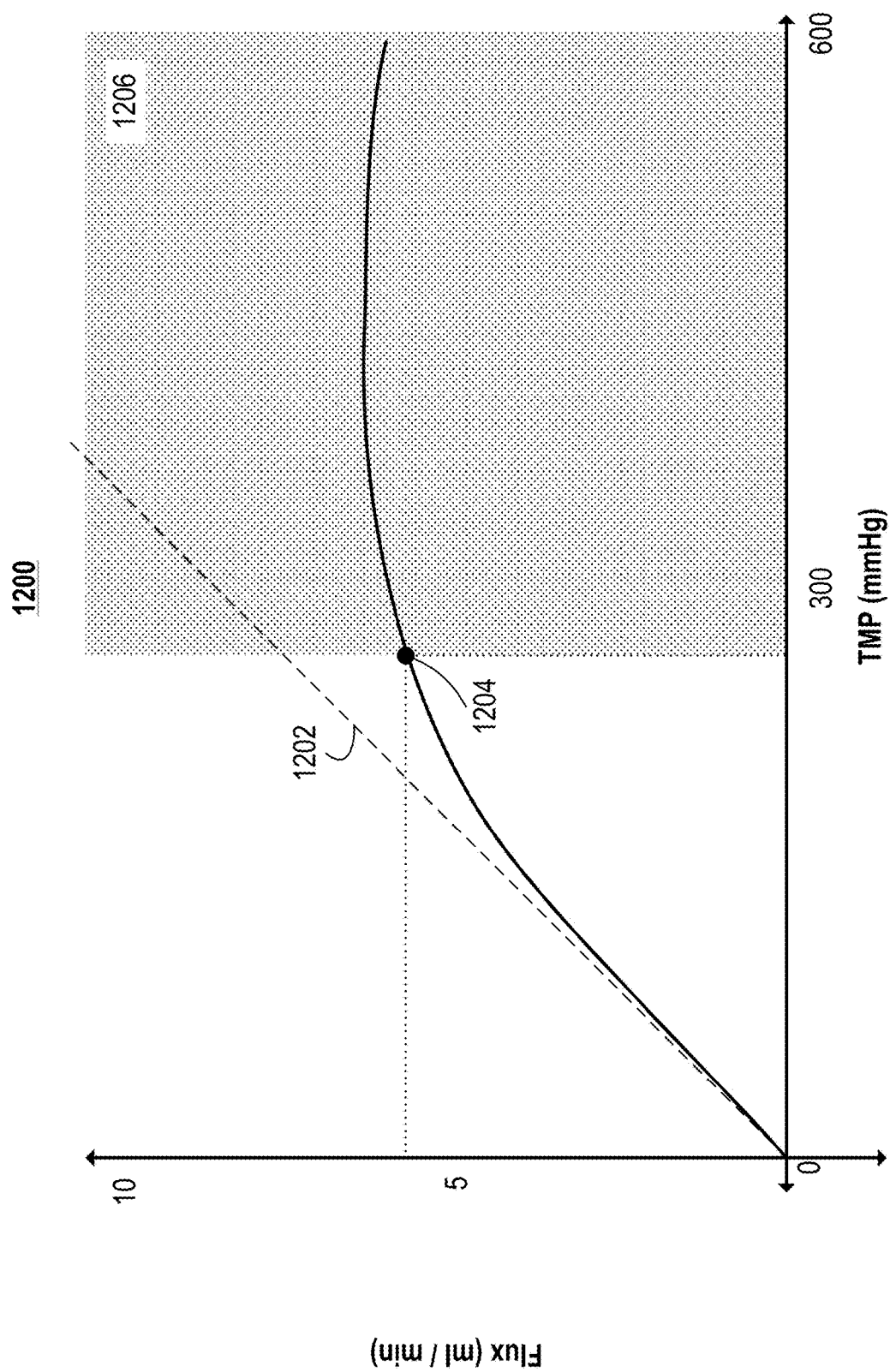
FIG. 12 illustrates a graph comparing example transmembrane pressures to the flux across a filtrate membrane in a microfluidic convective clearance device, such as that illustrated in FIGS. 5A and 5B.

FIG. 12 illustrates a graph 1200 comparing transmembrane pressure to the flux across the filtrate membrane. The graph 1200 illustrates that as the transmembrane pressure increases, the increase in flux is initially linear, as indicated by line 1202. At higher relative transmembrane pressures, the flux is non-linear, and in some cases can begin to decline. The decrease in the flux's slope as the transmembrane pressure increases can be attributed to the formation of a protein layer at the surface of the filtrate membrane. Increasing the transmembrane pressure past a "critical flux" point 1204 (also referred to as a critical transmembrane pressure 1204) can cause damage to the membrane's filtration capacity. As illustrated in FIG. 12, the critical flux point 1204 is at about 250 mmHg. The shaded region 1206 indicates transmembrane pressures past the critical flux point 1204 that may cause damage to the membrane. Increasing the flux past the critical flux point 1204 can result in permanent damage to the membrane's filtration capacity as the protein layer is compressed against the filtrate membrane and increases hydraulic resistance across the membrane. The hydraulic resistance increases because the proteins in the blood fill and clog the pores of the membrane or a strong gel layer forms on the surface of the membrane. In some implementations, the damage is irreversible. The location of the critical flux point 1204 along the flux curve (and the shape of the flux curve itself) is dependent on many factors, such as the shear rate of the fluid flowing through the channels, protein concentrations within the fluid, membrane properties, and channel size. Accordingly, FIG. 12 represents one example critical flux point 1204, and in other implementations, the critical flux point 1204 can occur at pressure greater than or less than that illustrated in FIG. 12. In some implementations, the critical flux point 1204 can be the point where the slope of the flux is about 50% less than the initial linear slope of the flux. In some implementations, the critical flux point 1204 is determined experimentally. For example, for a given system, the pressures can be cycled between a baseline and an elevated pressure. With each cycle the elevated pressure is increased with respect to the elevated pressure used in the previous cycle. The cycling process can be continued until a permanent reduction of flux is experienced upon returning to the baseline pressure. In another experimental example, the flux across the membrane is increased in discrete steps until the transmembrane pressure begins to rise without an accompanying increase in flux.

In some implementations, transmembrane pressure profiles between the blood channel and the filtrate channel can violate a critical transmembrane pressure, which can result in the device not functioning optimally. The pressure control features described herein can provide protection against violating a known critical transmembrane pressure. Controlling the pressure to not violate the known critical transmembrane pressure can improve membrane reliability and device durability. For example, one or more of the pressure control devices described herein can be used to limit the amount of pre-dilution bias or post-dilution bias. Limiting the pre- and post-dilution bias can enable the operation of the device without violating the critical transmembrane pressure along the length of the device. In some implementations, not substantially violating the critical transmembrane pressure improves the device's long-term durability. Improving the durability of the membrane can increase total filtrate production over the course of a treatment because the resistance across the membrane remains relatively low. In contrast, violating the critical transmembrane pressure can provide higher short-term filtrate flow, but can ultimately result in lower total filtrate production over the course of a treatment as the membrane's resistance increases during the treatment. In some implementations, the highest filtrate production is achieved in a device that is operating with parallel pressure profiles for the blood and filtrate channels with the average transmembrane pressure at or less than the critical transmembrane pressure. Operating the device in this case, can result in lower membrane and filter costs, and also less foreign body interaction between the blood and the filter components.

Figure 13:
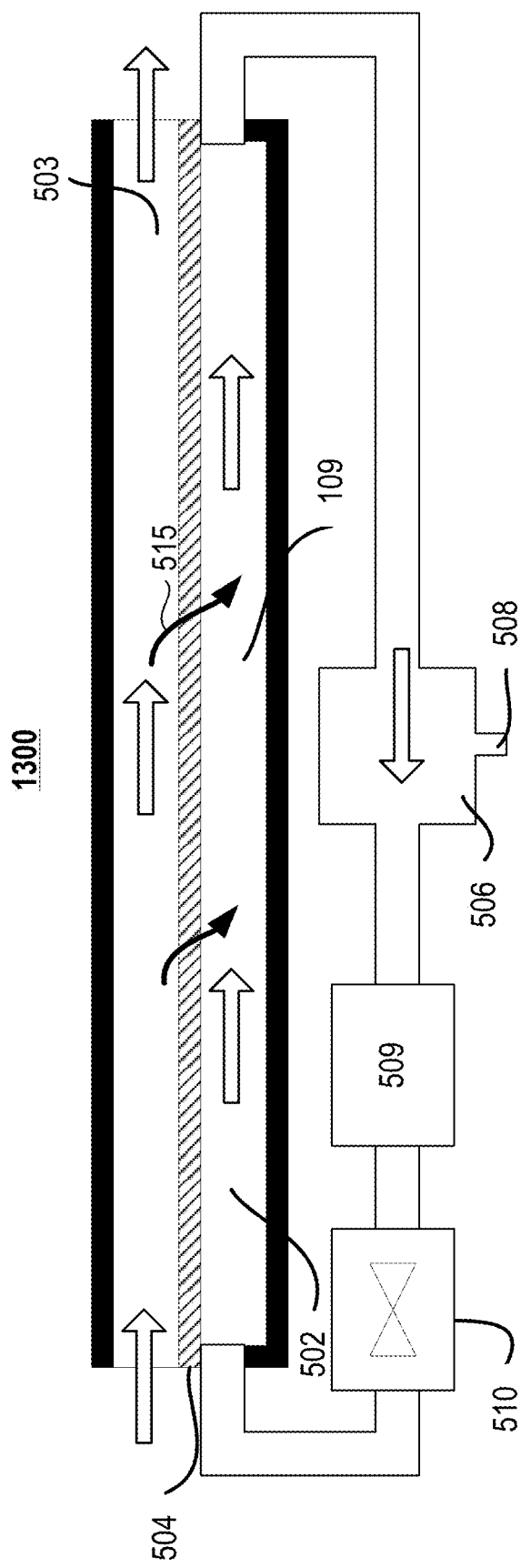
FIG. 13 illustrates a cross-sectional view of an example two-layer microfluidic convective clearance device for use in hemofiltration.

FIG. 13 illustrates a cross-sectional view of a microfluidic convective clearance device 1300 for use in hemofiltration. The device 1300 is a two-layer device that includes a blood flow channel 503 and a filtrate channel 502. In contrast to the device 500 describe above in relation to FIG. 5A, the device 1300 does not include a infusate channel 501. The device 1300 is configured to include any of the pressure control features described herein to maintain a predetermined pressure profile in the blood channel 503 and the filtrate channel 502. As described above in relation to device 500, the blood channel 503 is separated from the filtrate channel 502 by a membrane 504. The filtrate channel 502 is in fluid communication with a filtrate reservoir 506 via manifolds such as those described above in relation to FIG. 1A. A pump 509 is placed in-line with the filtrate reservoir 506. A valve 510 is placed in-line with the pump 509. In some implementations, passive and/or active pressure control features other than a valve 510 are placed in-line with the filtrate channel 502. For example, the pressure profile of the filtrate channel 502 can be controlled with a variable flow pump or a diaphragm chamber.

In some implementations, the control system of the device 1300 controls the operational state of the valve 510 to control the pressure profile of the filtrate channel 502. In some implementations, the control system controls the valve 510 (or other controllable flow control device) such that the difference between the filtrate channel's pressure profile and the blood channel's pressure profile is below a predetermined pressure. For example, the control system can control valve 510 to prevent the pressure difference between the blood channel's pressure profile and the filtrate channel's pressure profile from exceeding a critical transmembrane pressure. In one example, the control system may increase the inlet pressure of the filtrate channel to drive the pressure profile of the filtrate toward the pressure profile of the blood channel. As the pressure profile of the filtrate channel raises toward the pressure profile of the blood channel, the pressure difference reduces to stay below the critical transmembrane pressure. In another example, the control system may control the influx and outflow pumps to control the rate at which new filtrate is introduced and used filtrate is removed from the device 1300. The control system can also control other active pressure control systems, such as a variable flow pump and a diaphragm chamber.

Figure 14:
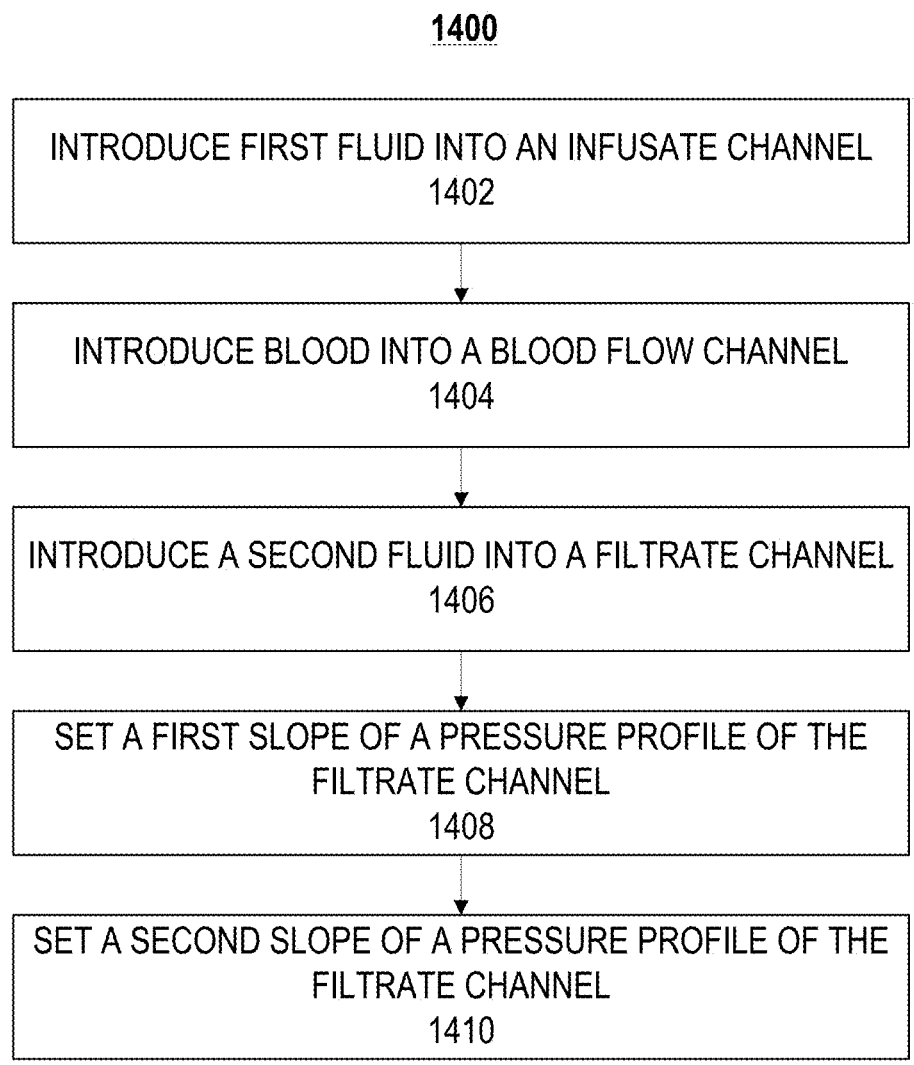
FIG. 14 illustrates a flow chart of an example method for cleansing a fluid using a microfluidic convective clearance device.

FIG. 14 illustrates a flow chart of an example method 1400 for cleansing a fluid. The method 1400 includes introducing a first fluid into an infusate channel (step 1402). The method 1100 also includes introducing blood into a blood flow channel (step 1404) and a filtrate into a filtrate channel (step 1406). A pressure control feature is used to set a first slope of the filtrate's pressure profile (step 1408). The pressure control feature is then used to set a second slope of the filtrate's pressure profile (step 1410).

As set forth above, the method 1400 includes introducing a first fluid into an infusate channel (step 1402). The infusate channel can be an infusate channel of any of the devices described herein, and the first fluid can be infusate. The method 1400 also includes introducing blood into a blood flow channel (step 1404). In some implementations, the blood and the infusate channels are parallel and complementary to one another. For example, the blood and the infusate channels overlap one another and are separated by a membrane or other interchannel flow barrier. In some implementations, the blood and the infusate are flowed through the device in the same direction. In some implementations, the infusate is introduced into the infusate channel at a relatively higher pressure than the blood is introduced to the blood flow channel.

The method 1400 also includes introducing a second fluid into the filtrate channel (step 1406). In some implementations, the second fluid is a filtrate. The filtrate channel can be any of the filtrate channels described herein. The filtrate can be flowed through the device in the same direction as the blood and insulate. In some implementations, the filtrate and the infusate are flowed in the opposite direction through the device with respect to the direction of the blood flow. In some implementations, the second fluid is a dialysate.

Each of the filtrate channel, blood channel, and infusate channel has a pressure profile along its length. The method 1400 also includes setting a first slope of the filtrate channel's pressure profile (step 1408). The slope of the pressure profile can be set with any of the controllable flow control devices described herein. For example, a desired pressure profile can be supplied to the system controller, which can control a pressure valve near the inlet of the filtrate channel to control the pressure of the filtrate entering the filtrate channel.

The method 1400 also includes setting a second slope of the filtrate channel's pressure profile (step 1410). The slope of the pressure profile can be set with any of the controllable flow control devices described herein. In some implementations, the first and the second slopes of the filtrate channel are set with respect to slope of the infusate channel's pressure profile or the blood channel's pressure profile. For example, the slope of the filtrate channel's pressure profile may initially be set to be less than the slope of the blood channel's pressure profile and then be set to be greater than the slope of the blood channel's pressure profile. In another implementation, the slope of the filtrate channel's pressure profile may initially be set to be greater than the slope of the blood channel's pressure profile and then be set to be less than the slope of the blood channel's pressure profile. In some implementations, the method 1400 also includes controlling the slope of the pressure profile of the infusate and blood channels.

The slope of each of the pressure profiles is controlled by the control system. The control system is configured to control each of the convective clearance device's controllable flow control devices. The controllable flow control devices can include any of a recirculating pump, a proportional valve, a diaphragm chamber, an influx pump, and an outflow pump. The control system controls the operational state of the controllable flow control device. For example, the control system may control a regulator coupled to a diaphragm chamber. By controlling the opening of the regulator, the control system can cause the introduction of pressure into the diaphragm chamber, which constricts the passageway through the diaphragm chamber and increases the pressure of the fluid exiting the diaphragm chamber. In some implementations, one or more of the channels in the convective clearance device includes a plurality of controllable flow control devices. For example, the infusate and filtrate channels can include a controllable flow control device positioned toward the inlet and the outlet of each channel.

In some implementations, the control system receives pressure measurements from pressure sensors placed along the length of any of the filtrate, blood, and infusate channels. For example, each of the channels can include a plurality of pressure sensors distributed along the length of each of the channels. In some implementations, the pressure sensors are placed toward the inlet and outlet of any of the filtrate, blood, and infusate channels. The control system uses the pressure measurements from the pressure sensors to form a feedback loop to maintain the set slopes of each of the pressure profiles.

In some implementations, the control system maintains a predetermined pressure difference between the pressure profile of the filtrate channel and the pressure profile of the blood channel. The control system can receive pressure measurement from the pressure sensors placed along the length of the blood and filtrate channels to ensure that the pressure difference remains below a critical transmembrane pressure along the length of the device.

The disclosed system and methods may be embodied in other specific forms without departing from the spirit or essential characteristics thereof. The forgoing implementations are therefore to be considered in all respects illustrative, rather than limiting of the invention.

As utilized herein, the terms "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

What is claimed:

1. A microfluidic device comprising:
   a first layer defining an infusate channel, the infusate channel having a first pressure profile with a first slope along a length of the infusate channel;
   a second layer defining a blood channel in fluidic communication with the infusate channel, the blood channel having a second pressure profile with a second slope along a length of the blood channel;
   a filtrate layer defining a filtrate channel in fluidic communication with the blood channel, the filtrate channel having a third pressure profile with a third slope along a length of the filtrate channel;
   a first interchannel flow barrier separating the infusate channel and the blood channel, wherein the first interchannel flow barrier includes a plurality of openings defined through the first interchannel flow barrier, allowing passage of fluid from the infusate channel into the blood channel;
   a second interchannel flow barrier separating the filtrate channel and the blood channel;
   a first controllable flow control device along a length of the filtrate channel configured to actively control the third slope of the third pressure profile along the length of the filtrate channel relative to the second slope of the second pressure profile along the length of the blood channel;
   a second controllable flow control device configured to actively control the first slope of the first pressure profile along the length of the infusate channel relative to the second slope of the second pressure profile along the length of the blood channel; and
   a control system configured to modify a state of the first controllable flow control device and the second controllable flow control device such that the first slope of the first pressure profile along the length of the infusate channel is substantially parallel to the third slope of the third pressure profile along the length of the filtrate channel.

2. The microfluidic device of claim 1, further comprising at least one pressure sensor coupled to the control system, wherein the control system is configured to modify the state of the first or second controllable flow control device responsive to an output of the at least one pressure sensor.

3. The microfluidic device of claim 1, wherein the first and second controllable flow control devices are one of a recirculating pump, a proportional valve, a diaphragm chamber, or an outflow pump.

4. The microfluidic device of claim 1, wherein the control system is configured to control the first and second controllable flow control devices such that the first pressure profile is substantially parallel to the second pressure profile.

5. The microfluidic device of claim 1, wherein the control system is configured to cause the first controllable flow control device to achieve a state such that the slope of the third pressure profile is greater than the slope of the second pressure profile.

6. The microfluidic device of claim 1, wherein the control system is configured to cause the first controllable flow control device to achieve a state such that the slope of the third pressure profile is less than the slope of the second pressure profile.

7. The microfluidic device of claim 1, comprising a third controllable flow control device configured to, along with the first controllable flow control device, actively control the slope of the third pressure profile along the length of the filtrate channel relative to the slope of the second pressure profile along the length of the blood channel.

8. The microfluidic device of claim 1, wherein the blood channel has a height in the range of about 50 µm to about 500 µm, a width in the range of about 50 µm to about 900 µm, and a length in the range of about 3 cm to about 30 cm.

9. The microfluidic device of claim 1, wherein the second interchannel flow barrier comprises a membrane.

10. The microfluidic device of claim 1, wherein the second interchannel flow barrier is a sterility barrier.

11. The microfluidic device of claim 1, wherein the first interchannel flow barrier further comprises a membrane located between the infusate channel and the blood channel.

12. The microfluidic device of claim 1, wherein the second layer defines a plurality of blood channels.

13. The microfluidic device of claim 12, wherein the plurality of blood channels are in fluid communication with the infusate channel through the plurality of openings in the first interchannel flow barrier.

14. The microfluidic device of claim 13, wherein the plurality of openings through the first interchannel flow barrier are positioned sequentially along the length of the infusate channel, and each of the openings spans across all of the blood channels in the second layer.

15. The microfluidic device of claim 14, wherein the openings through the first interchannel flow barrier have a pitch along the length of the infusate channel of between about 1 cm and 10 cm.

16. The microfluidic device of claim 14, wherein the spacing of the openings through the first interchannel flow barrier decreases along the length of the infusate channel.

17. The microfluidic device of claim 14, wherein the size of the openings through the first interchannel flow barrier increases along the length of the infusate channel.

18. The microfluidic device of claim 1, wherein the first interchannel flow barrier comprises a substantially non-porous material through which the openings are defined.

19. The microfluidic device of claim 18, wherein the first interchannel flow barrier includes a portion of the first layer defining a floor of the infusate channel.

* * * * *